US010012758B2

(12) United States Patent
Speck et al.

(10) Patent No.: US 10,012,758 B2
(45) Date of Patent: Jul. 3, 2018

(54) SOLID STATE LASERS

(71) Applicant: Schlumberger Technology Corporation, Sugar Land, TX (US)

(72) Inventors: Andrew J. Speck, Milton, MA (US); A. Ballard Andrews, Wilton, CT (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 539 days.

(21) Appl. No.: 14/365,103

(22) PCT Filed: Dec. 6, 2012

(86) PCT No.: PCT/US2012/068125
§ 371 (c)(1),
(2) Date: Jun. 12, 2014

(87) PCT Pub. No.: WO2013/090108
PCT Pub. Date: Jun. 20, 2013

(65) Prior Publication Data
US 2014/0339412 A1  Nov. 20, 2014

Related U.S. Application Data

(60) Provisional application No. 61/570,550, filed on Dec. 14, 2011.

(51) Int. Cl.
*G01V 8/02* (2006.01)
*H01S 3/06* (2006.01)
(Continued)

(52) U.S. Cl.
CPC ............ *G01V 8/02* (2013.01); *G01N 21/255* (2013.01); *G01N 21/65* (2013.01); *G01N 21/718* (2013.01);
(Continued)

(58) Field of Classification Search
CPC .... G01N 21/65; G01N 21/255; G01N 21/256; G01N 21/718; G01V 8/02; H01S 3/0627; H01S 3/113
See application file for complete search history.

(56) References Cited

U.S. PATENT DOCUMENTS 4,577,110 A    3/1986  MacBride et al.
5,867,266 A    2/1999  Craighead
(Continued)

FOREIGN PATENT DOCUMENTS

JP    2009540582 A    11/2009
WO   2011147620 A1   12/2011

OTHER PUBLICATIONS

Partial European Search Report issued in equivalent European Application No. 12857402.7 dated Oct. 2, 2015 (5 pages).
(Continued)

*Primary Examiner* — David Porta
*Assistant Examiner* — Mindy Vu
(74) *Attorney, Agent, or Firm* — Michael Dae

(57) ABSTRACT

Solid state lasers are disclosed herein. An example laser disclosed herein includes a monolithic body having a first end and a second end. The monolithic body includes a first reflector disposed on the first end, a second reflector disposed on the second end, and a solid state gain medium and a Q-switch disposed between the first reflector and the second reflector. The example laser also includes a pump source to cause a population inversion in the solid state gain medium to cause the monolithic body to output a laser pulse. Various applications of the solid state laser are also disclosed herein.

8 Claims, 18 Drawing Sheets

(51) Int. Cl.
*H01S 3/113* (2006.01)
*G01N 21/65* (2006.01)
*G01N 21/25* (2006.01)
*G01N 21/71* (2006.01)
*H01S 3/093* (2006.01)
*H01S 3/0933* (2006.01)
*H01S 3/00* (2006.01)
*G01N 21/85* (2006.01)

(52) U.S. Cl.
CPC ............ *H01S 3/0627* (2013.01); *H01S 3/113* (2013.01); *G01N 21/8507* (2013.01); *H01S 3/0092* (2013.01); *H01S 3/0931* (2013.01); *H01S 3/0933* (2013.01)

(56) References Cited

U.S. PATENT DOCUMENTS

| | | | |
|---|---|---|---|
| 6,507,401 B1* | 1/2003 | Turner | E21B 47/102 356/417 |
| 6,590,647 B2 | 7/2003 | Stephenson | |
| 7,114,562 B2 | 10/2006 | Fisseler et al. | |
| 7,719,676 B2 | 5/2010 | DiFoggio | |
| 7,821,635 B2 | 10/2010 | Pope et al. | |
| 8,786,840 B1 | 7/2014 | Woodruff et al. | |
| 2002/0094007 A1 | 6/2002 | Brian et al. | |
| 2003/0169414 A1 | 9/2003 | Paul et al. | |
| 2005/0084912 A1* | 4/2005 | Poponin | B82Y 20/00 435/7.1 |
| 2007/0076199 A1 | 4/2007 | Ode | |
| 2007/0081157 A1 | 4/2007 | Csutak et al. | |
| 2008/0111064 A1 | 5/2008 | Andrews et al. | |
| 2008/0149819 A1 | 6/2008 | Oleg | |
| 2008/0247425 A1 | 10/2008 | David | |
| 2010/0044103 A1* | 2/2010 | Moxley | E21B 7/14 175/16 |
| 2010/0195679 A1 | 8/2010 | Gerhard et al. | |
| 2014/0209794 A1 | 7/2014 | Woodruff et al. | |

OTHER PUBLICATIONS

M.L. Shand and H.P. Jenssen, "Temperature Dependence of the Excited-Stae Absorption of Alexandrite," IEEE Journal of Quantum Electronics, 19(3), pp. 480-484, 1983.

T. Sun, et al., "Analysis of the double exponential behavior in alexandrite for optical temperature sensing applications," Review of Scientific Instruments, 68(9), pp. 3442-3446, 1997.

A. Rapaport, et al., "Temperature Dependence of the 1.06-micrometer Stimulated Emission Cross Section of Neodymium in YAG and in GSGG," Applied Optics, 41 (33), pp. 7052-7057, 2002.

T. Dascalu and N. Pavel, "High-Temperature Operation of a Diode-Pumped Passively Q-Switched Nd: YAG/Cr, YAG Laser," Laser Physics, 19 (11), pp. 2090-2095, 2009.

F. Trager, "Springer Handbook of Lasers and Optics," Springer, New York 2007.

W. Koechner, "Solid-State Laser Engineering," 6th ed. Springer, New York, 2006.

International Search Report and Written Opinion issued in the related PCT Application PCT/US2012/068125, dated Mar. 29, 2013 (12 pages).

International Preliminary Report on Patentability issued in the related PCT Application PCT/US2012/068125, dated Jun. 14, 2014 (8 pages).

Extended European Search Report issued in the related EP Application 12857402.7, dated Jan. 18, 2016 (11 pages).

Background Filtering in Fiber Optic Raman Sampling Probes, Technical Note # 3, InPhotonics (2 pages).

Office action issued in the related JP application 2014547298, dated Sep. 29, 2016 (8 pages).

* cited by examiner

SOLID STATE LASERS

PRIORITY

The present application claims the benefit of U.S. Application Ser. No. 61/570,550, filed Dec. 14, 2011, which application is incorporated herein, in its entirety, by reference.

BACKGROUND OF THE DISCLOSURE

Generally, a laser includes a gain medium (e.g., a gas, liquid, solid, or plasma) and an energy supply. The gain medium often absorbs energy (e.g., optical radiation, electrical current, kinetic energy, thermal energy, etc.) from the energy supply. The energy may excite atoms in the gain medium until a population inversion occurs (i.e., a number of electrons in an excited state exceeds a number of electrons in a relatively lower energy state). If the population inversion occurs, the gain medium generally emits more photons than the gain medium absorbs. If an electromagnetic wave (e.g., visible light) interacts with the gain medium during the population inversion, the gain medium may amplify the electromagnetic wave, and the laser may output a laser pulse.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Illustrative embodiments of the present disclosure are directed to a laser. The laser includes a monolithic body having a first end and a second end. The monolithic body includes a first reflector disposed on the first end, a second reflector disposed on the second end, and a solid state gain medium and a Q-switch disposed between the first reflector and the second reflector. The example laser also includes a pump source to cause a population inversion in the solid state gain medium that causes the monolithic body to output a laser pulse.

Illustrative embodiments of the present disclosure are also directed to a method for using a laser. The method includes disposing a laser in an environment in which a temperature is greater than one hundred degrees Celsius. The laser includes a monolithic body having a first reflector, a second reflector, and a solid state gain medium disposed between the first reflector and the second reflector. The example method further includes energizing a pump source to cause a population inversion in the solid state gain medium that causes the laser to output a laser pulse.

In a further embodiment, as described herein, an example laser includes a solid state gain medium having a first end and a second end. The example laser also includes a retroreflector adjacent the first end of the solid state gain medium and a reflector adjacent the second end of the solid state gain medium. The example laser further includes a pump source to cause a population inversion in the solid state gain medium. The solid state gain medium outputs a laser pulse through the reflector. The laser pulse has a pulse energy substantially independent of temperature when exposed to temperatures between about room temperature and about two hundred degrees Celsius.

Further illustrative embodiments of the disclosure are directed to a system for optically analyzing a sample. The system includes a pulsable laser that outputs a beam of light. A window is disposed between the laser and the sample. A micro lens array (or arrays) directs and focuses the beam of light through the window onto the sample. A detector detects light that interacts with the sample. The light that interacts with the sample is directed onto the detector by the second optical member and a third optical member.

In yet another embodiment of a system for optically analyzing a sample. The system includes a pulsable laser to output a beam of light. A window is disposed between the laser and the sample. The example system also includes a first optical member and a second optical member to collimate the beam of light outputted by the laser and direct the beam of light through the window onto the sample. The example system further includes a detector to determine a characteristic of the sample based on light interacting with the sample. The light interacting with the sample is directed onto the detector by the first optical member and the second optical member.

Illustrative embodiments of the disclosure are further directed to a downhole production logging tool for analyzing formation fluid. The tool includes a tool housing with a window. The tool also includes an optical module (e.g., a spectrometer) for analyzing the formation fluid. The optical module includes a light source that outputs light and an optical member (or members) that direct the light through the window into the formation fluid outside of the tool housing. The module also includes a detector that detects the light that interacts with the formation fluid and passes back through the window.

BRIEF DESCRIPTION OF THE DRAWINGS

Illustrative embodiments are described with reference to the following figures.

DETAILED DESCRIPTION

Figure 1:
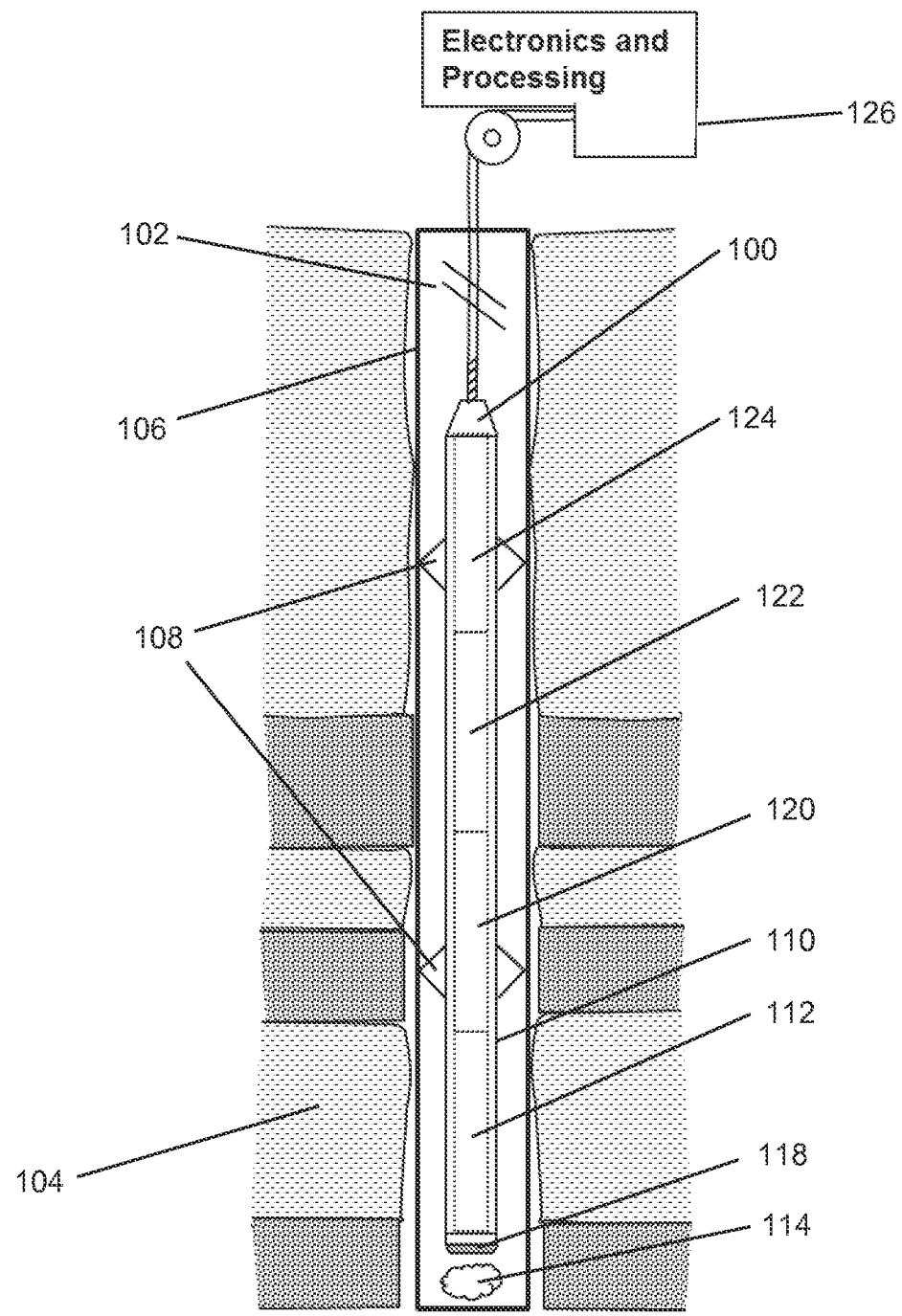
FIG. 1 illustrates a production logging tool in which embodiments of the example solid state lasers can be implemented.

It is to be understood that the following disclosure provides many different embodiments or examples for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features such that the first and second features may not be in direct contact.

One or more aspects of the present disclosure relate to solid state lasers. An example laser disclosed herein includes a monolithic body having a first end and a second end. The monolithic body includes a first reflector disposed on the first end and a second reflector disposed on the second end. The monolithic body also includes a solid state gain medium. The solid state gain medium may be disposed between the first reflector and the second reflector. The solid state gain medium may be a material in a solid state such as, for example, a chromium doped beryllium aluminum oxide crystal ($Cr^{3+}:BeAl_2O_4$) ("alexandrite"), a neodymium-doped yttrium aluminum garnet crystal ($Nd:Y_3Al_5O_{12}$) ("Nd:YAG") or any other suitable material. In some examples, the monolithic body includes a Q-switch.

The example laser also includes a pump source (e.g., a flash lamp, an arc lamp, a light emitting diode (LED), a diode laser, etc.). In some examples, the laser may include a reflective cavity substantially enclosing the monolithic body and the pump source. During operation, the pump source emits light. The light emitted from the pump source may cause a population inversion (e.g., a number of electrons in an excited state exceed a number of electrons in a relatively lower energy state) in the solid state gain medium, and the example laser may output a laser pulse through the second reflector. The example laser may advantageously output the laser pulse even when the laser is subjected to shocks (e.g., a 500 g shock) and/or vibrations (e.g., a 0.5 g^2/√Hz vibration). In some examples, a pulse energy of the laser pulse may be substantially constant when the laser is exposed to temperatures between about room temperature and about 200° C.

Illustrative embodiments of the present disclosure are directed to oil field and gas field borehole applications. FIG. 1 shows an example of a downhole tool 100 that incorporates an embodiment of a laser as described herein. In this case, the downhole tool 100 is a production logging tool that is disposed within a borehole 102 that traverses an earth formation 104. The borehole 102 includes a casing 106 and the production logging tool 100 is lowered into the casing 106 via a wireline cable and centered within the casing using a set of centralizers 108. During production logging, formation fluid (e.g., formation liquid and/or formation gas) is extracted from different pay zones of the earth formation 104. As the formation fluid flows to the surface, the production logging tool 100 can be used to monitor the characteristics of the fluid (e.g., composition). As shown in FIG. 1, the production logging tool 100 includes a housing 110 that houses a plurality of modules. At one end, the housing 110 includes an optical module 112 for performing spectroscopic measurements on a sample of the formation fluid 114 (e.g., Raman spectroscopy, and laser induced breakdown spectroscopy). The optical module 112 includes optics, at least one detector, and a light source, such as a laser, that correspond with the embodiments described herein. The laser generates light that is used to analyze the sample of formation fluid 114. The light that scatters back from the sample is detected by the detector. The optics are used to communicate the light to and from the sample 114. The optical module 112 is in optical communication with the borehole fluid via a window 118. In this manner, the sample of formation fluid 114 adjacent the window 118 is analyzed by the optical module 112. In this case, the window 118 is located at the lower end of the tool. In additional or alternative embodiments, the window is located on a sidewall of the housing 110. In yet another embodiment, one window is located at the end of the housing 110 and a second window is located on the side of the housing 110.

The production logging tool 100 also includes several other modules that support the optical module 112. For example, the production logging tool 100 includes a power module 120 to provide power to the laser and the detector. Also, the production logging tool 100 may include an amplification module 122 to amplify an electrical signal that is output from the optical module. This electrical signal is representative of light scattered back from the sample and detected by the detector. Furthermore, the production logging tool may include a telemetry system 124 to provide communication between the production logging tool and surface electronics and processing systems 126. In one example, the telemetry system 124 communicates the electrical signal from the optical module 112 to the surface.

In one specific application, the production logging tool 100 is used in a gas condensate well. The pressures, temperatures, and fluid densities encountered in gas condensate wells produce a multi-phase flow with a phase separation as the gas and liquid flow to the surface. The phase separation produces an annular flow pattern with the gas fraction flowing in the middle of the casing and the fluid fraction flowing against the sides of the casing. Centralizers 108, as shown in FIG. 1, allow the gas fraction to be separately sampled, avoiding interference from the fluid fraction. The optical module 112 described herein can analyze various different types of gases. Exemplary gases include but are not limited to methane, ethane, propane, carbon dioxide, hydrogen sulfide, and nitrogen. In one specific embodiment, a Raman spectroscopy technique is used determine the composition of the gas fraction in the condensate well. In particular, the Raman spectroscopy technique uses a laser light signal and detects a response within the gas fraction this is linear in the density of the gas fraction.

In one embodiment of the tool, a back scattering geometry is employed, in which an axis of the excitation beam is collinear with an axis of the detected light. This back scattering geometry is advantageous for production logging because the composition of the fluid fractions may be determined without passing the fluid or gas fraction through a flow line. Illustrative embodiments of the tool are not limited to a back scattering geometry. In other embodiments, the axis of the excitation beam is offset from the axis of the detected light (e.g., spatially and/or angularly).

Figure 2:
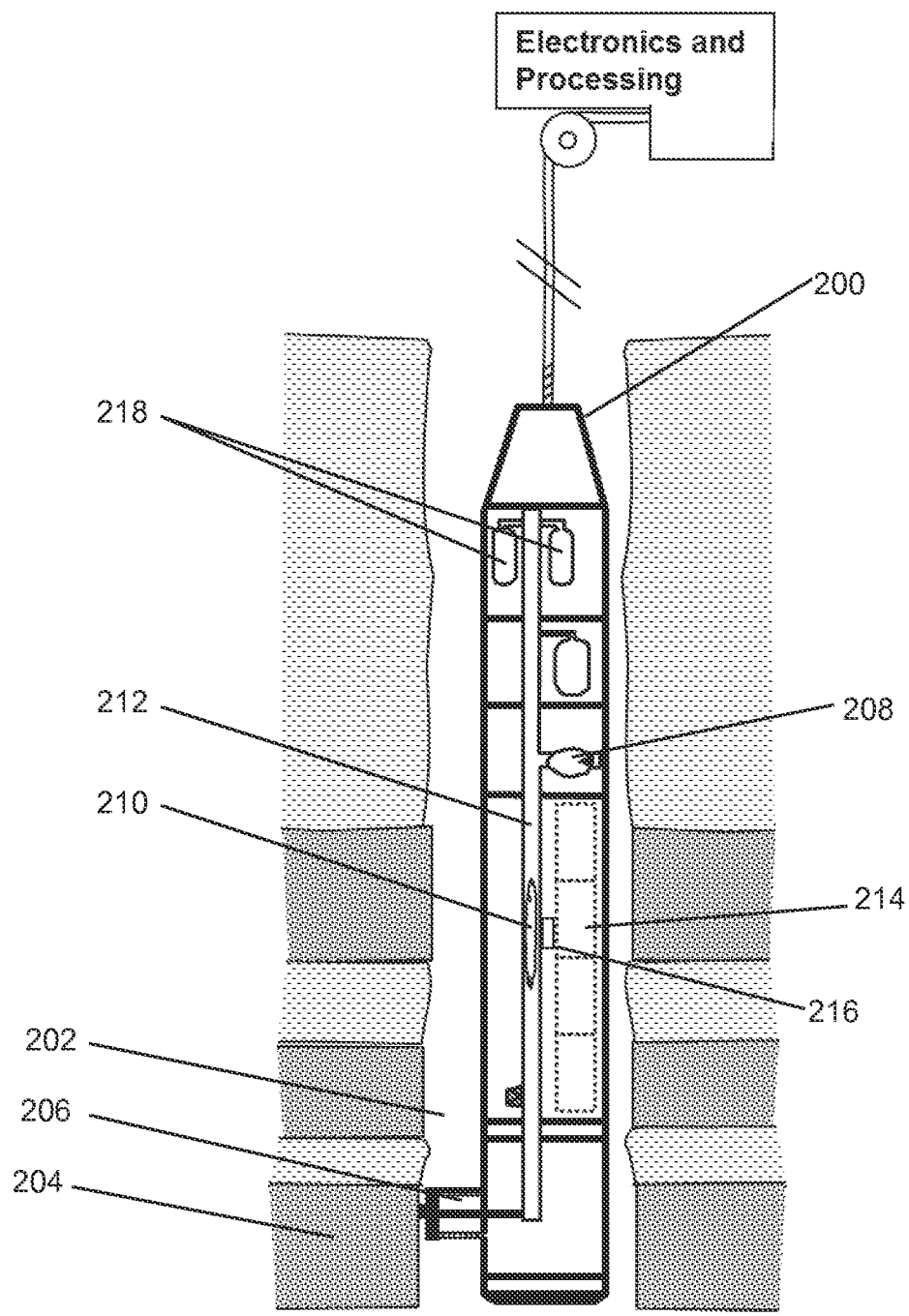
FIG. 2 illustrates a wireline tool in which embodiments of the example solid state lasers can be implemented.

FIG. 2 shows an example of another downhole tool 200 that incorporates an embodiment of a laser. In this particular embodiment, the downhole tool 200 is a wireline tool. The wireline tool 200 is suspended within a borehole 202 that traverses an earth formation 204. The tool 200 is suspended within the borehole using a multiconductor cable that is spooled on a winch at the surface. In contrast to the embodiment of FIG. 1, in which the formation fluid sample is analyzed outside the downhole tool 100, in this embodiment, the wireline tool 200 draws a fluid sample (e.g., formation fluid or borehole fluid) into the tool and analyzes the sample within the tool. In a specific embodiment, the fluid sample is a gas. To this end, the wireline tool 200 includes a formation tester 206 having a selectively extendable probe assembly. The extendable probe assembly is configured to fluidly couple to an adjacent formation 204 and to draw fluid samples from the formation. A pump 208 is used to pass a fluid sample 210 through the probe assembly and into a flow line 212 within the tool 200.

The wireline tool 200 also includes an optical module 214 for performing spectroscopic measurements on the fluid sample 210 within the flow line 212. (e.g., Raman spectroscopy, absorption spectroscopy and laser induced breakdown spectroscopy). The optical module 214 includes a laser, optics and at least one detector that correspond with the embodiments described herein. The optical module 214 is in optical communication with the fluid sample 210 within the flow line 212 via a window 216. In this manner, the fluid sample 210 within the flow line 212 is analyzed by the optical module 214. Once the fluid sample 210 is analyzed, the sample can be expelled through a port (not shown) or the sample may be sent to one or more fluid collecting chambers 218.

Various embodiments of the present disclosure are not limited to the production logging tool 100 and the wireline tool 200 shown in FIGS. 1 and 2. For example, in another embodiment, a wireline tool may include a window and an optical module for analyzing fluid samples within the borehole and outside the tool, in a similar manner to the production logging tool 100 of FIG. 1. Illustrative embodiments of the present disclosure can also be used in drilling applications, such as logging-while-drilling (LWD) systems or measuring-while-drilling (MWD) systems. In one particular embodiment, the LWD system includes a sampling-while-drilling system (e.g., the sampling-while-drilling system is part of an LWD tool suite). In such a sampling-while-drilling system, a fluid sample is drawn into the system from the formation and analyzed within the tool, in a similar manner to the wireline tool 200 of FIG. 2. Further details of sampling-while-drilling systems are provided in U.S. Pat. No. 7,114,562, entitled "Apparatus and Method for Acquiring Information while Drilling."

Figure 3:
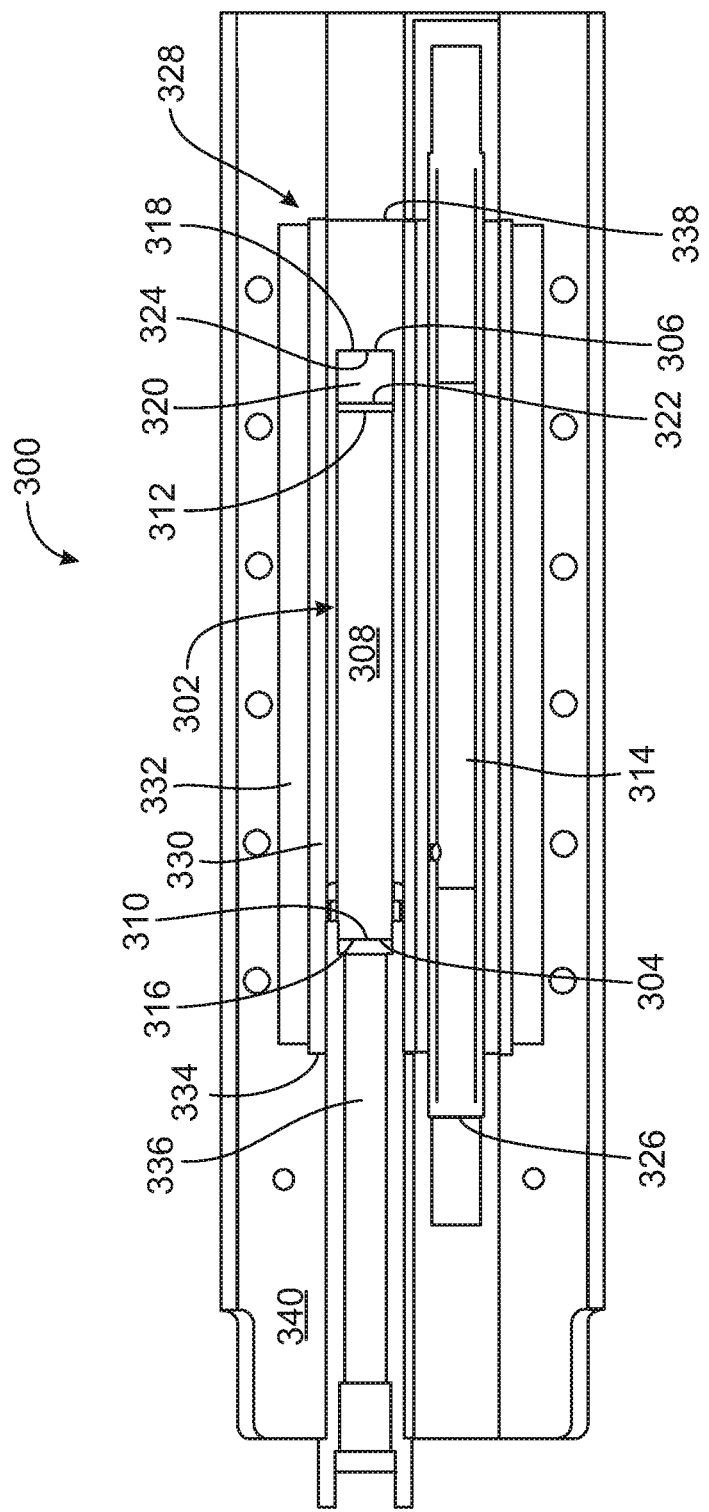
FIG. 3 illustrates various components of an example device that can implement embodiments of the example solid state lasers.

FIG. 3 is a cross-sectional view of a laser 300 disclosed herein. The example laser 300 of FIG. 3 may be employed to provide a light source for a variety of spectroscopy techniques (e.g., Raman spectroscopy, absorption spectroscopy, laser induced breakdown spectroscopy, etc.). The laser 300 includes a monolithic body 302 having a first end 304 and a second end 306. The first end 304 and the second end 306 may be polished. In some examples, the monolithic body 302 is rod-shaped. The monolithic body 302 includes a solid state gain medium 308 having a first end 310 and a second end 312. The solid state gain medium 308 is a material in a solid state such as, for example, a chromium doped beryllium aluminum oxide crystal ($Cr^{3+}$:$BeAl_2O_4$) ("alexandrite"), a neodymium-doped yttrium aluminum garnet crystal (Nd:$Y_3Al_5O_{12}$) ("Nd:YAG"), or any other suitable material. Some example solid state gain media include dopant elements such as Nd, Yb, Er, Ti, Tm, and/or any other suitable dopant element. As described in greater detail below, the solid state gain medium 308 provides a photon gain when a pump source 314 creates a population inversion in the solid state gain medium 308.

A first reflector 316 and a second reflector 318 are disposed on the first end 304 and the second end 306 of the monolithic body 302, respectively. Thus, the example solid state gain medium 308 is disposed between the first reflector 316 and the second reflector 318. The first reflector 316 and the second reflector 318 provide an optical resonator (i.e., reflect light in a closed path). In the illustrated example, the first reflector 316 is disposed on the first end 310 of the solid state gain medium 308. In some examples, the first and second reflectors 316 and 318 are diffusion bonded to the first and second ends 304 and 306 to form the monolithic body 302, respectively. In some examples, the first and second reflectors 316 and 318 are film coatings. The example first reflector 316 has a reflectivity of about 100 percent (e.g., 95%, 98%, 99%, 99.9%, etc.) to reflect light emitted from the solid state gain medium 308. The example second reflector 318 has a reflectivity of less than 100 percent (e.g., 80%, 90%, etc.) to enable a laser pulse to pass through the second reflector 318. In some examples, the reflective surfaces of the first reflector 316 and the second reflector 318 are substantially parallel to each other. In other examples, the first reflector 316 and the second reflector 318 are curved. In some such examples, the first reflector 316 and the second reflector 318 are curved such that the first reflector 316 and the second reflector 318 are substantially confocal (i.e., radii of curvatures of the first reflector 316 and the second reflector 318 are equal to a distance between the first reflector 316 and the second reflector 318) or substantially concentric (i.e., the radii of curvatures of the first reflector 316 and the second reflector 318 are equal to half of the distance between the first reflector 316 and the second reflector 318).

The monolithic body 302 of the laser 300 includes a Q-switch 320. In some examples, such as the example illustrated in FIG. 3, the Q-switch 320 is a passive Q-switch such as, for example, a saturable absorber. A coefficient of thermal expansion of the Q-switch 320 may be substantially equal to a coefficient of thermal expansion of the solid state gain medium 308. In some examples, the Q-switch 320 is implemented using a Cr:YAG crystal. One end 322 of the Q-switch 320 may be non-adhesively bonded (e.g., diffusion bonded, optical contact bonded, etc.) to the second end 312 of the solid state gain medium 308. In some such examples, the second reflector 318 is disposed on an opposing end 324 of the Q-switch 320. Some embodiments of the laser do not include the Q-switch 320. In such examples, the second reflector 318 is disposed on the second end 312 of the solid state gain medium 308. As described in greater detail below, the Q-switch 320 prevents the laser from outputting a laser pulse until a population inversion in the solid state gain medium 308 reaches a predetermined level (e.g., a peak level).

In the illustrated example, the pump source 314 is a lamp pump source such as, for example, a flash lamp and/or an arc lamp. In other examples, the pump source 314 is a light emitting diode, a diode laser, and/or any other suitable pump source. The example pump source of FIG. 3 is adjacent the monolithic body 302. In some examples, longitudinal axes of the pump source 314 and the solid state gain medium 308 are substantially parallel to each other. In the illustrated example, the pump source 314 includes a substantially transparent tube 326 (e.g., glass, quartz, etc.) filled with a gas (e.g., Xenon, krypton, etc.). The pump source 314 is coupled to an electrical power source (e.g., a capacitor) (not shown). During operation, an electric current is delivered to the gas via the electrical power source to cause the gas to ionize and an arc to form through the gas. In some examples, the pump source 314 has an arc length of about 50 mm. The above-noted dimension is merely one example and, thus, other dimensions may be used without departing from the scope of this disclosure. The arc emits a flash of light such as, for example, a 100 μs flash of light. In other examples, the arc continuously emits light. In some examples, a temperature of the arc is about 10,000° C.

In the illustrated example, a reflective cavity 328 substantially encloses the monolithic body 302 and the pump source 314. The example reflective cavity 328 is defined by a substantially transparent (e.g., glass) cylinder 330 at least partially covered by a diffuse reflector 332 such as, for example, barium sulfate, Teflon®, and/or any other suitable diffuse reflector. In some examples, the reflective cavity 328 is an elliptical mirror. A first end 334 of the example reflective cavity 328 includes an aperture (not shown) adjacent the first end 304 of the monolithic body 302. A mount 336 extends through the aperture to hold and/or substantially align the monolithic body 302 in the reflective cavity 328. In some examples, the mount 336 holds the first end 304 of the monolithic body 302. In some examples, another mount extends through another aperture of the reflective cavity 328 and holds the monolithic body 302 along the Q-switch 320.

A second end 338 of the reflective cavity 328 is at least partially transparent and/or includes an aperture to enable the laser 300 to output a laser pulse through the second end 338 of the reflective cavity 328. In the illustrated example, the reflective cavity 328 and the mount 336 are disposed in a housing 340. The example mount 336 is coupled to the housing 340. The housing 340 may be disposed within a downhole tool such as, for example, the downhole tool of FIG. 1, the example tool of FIG. 2, or any other suitable downhole tool. In some examples, the laser 300 is employed at or near a surface of the Earth (e.g., in a laboratory).

During operation, the pump source 314 supplies energy to the solid state gain medium 308 by emitting light. The light emitted by the pump source 314 is reflected by the diffuse reflector 332 of the reflective cavity 328. The light excites atoms in the solid state gain medium 308 until a population inversion occurs in the solid state gain medium 308 (i.e., a number of electrons in an excited state exceed a number of electrons in a lower energy state). When the population inversion occurs, the solid state gain medium 308 emits more photons than the solid state gain medium 308 absorbs. As a result, the photons emitted by the solid state gain medium 308 are amplified by the reflective cavity 328 and the first and second reflectors 316 and 318 to cause a laser pulse to be transmitted through the second reflector 318.

During operation, the Q-switch 320 prevents the laser 300 from outputting or transmitting the laser pulse until the population inversion in the solid state gain medium 308 reaches a predetermined level (e.g., a peak level). For example, the Q-switch 320, a saturable absorber, is substantially non-transparent until the population inversion reaches the predetermined level. Once the population inversion reaches the predetermined level, the Q-switch 320 becomes at least partially transparent and the laser pulse passes through the Q-switch 320 and the second reflector 318.

When the laser 300 is exposed to temperatures between about room temperature and about 200° C., the laser 300 outputs laser pulses having pulse energies (e.g., 8 mJ, 14 mJ, 22 mJ, etc.) substantially independent of the temperatures. For example, from about room temperature to about 200° C., the laser 300 outputs laser pulses having pulse energies with a standard deviation within about 10 percent. The deviations are substantially attributable to random fluctuations that occur during operation regardless of the temperatures between about room temperature and about 200° C. such as, for example, creation of the arc in the pump source 314, recombination and continuum emission events producing light via the arc, and emitted photon directions from the events. Thus, the laser 300 outputs laser pulses having substantially constant pulse energies when exposed to temperatures between about room temperature and about 200° C. Also, the laser 300 advantageously outputs the laser pulses even when subjected to shocks (e.g., a 500 g shock) and/or vibrations (e.g., a 0.5 g^2/√Hz vibration).

Figure 4:
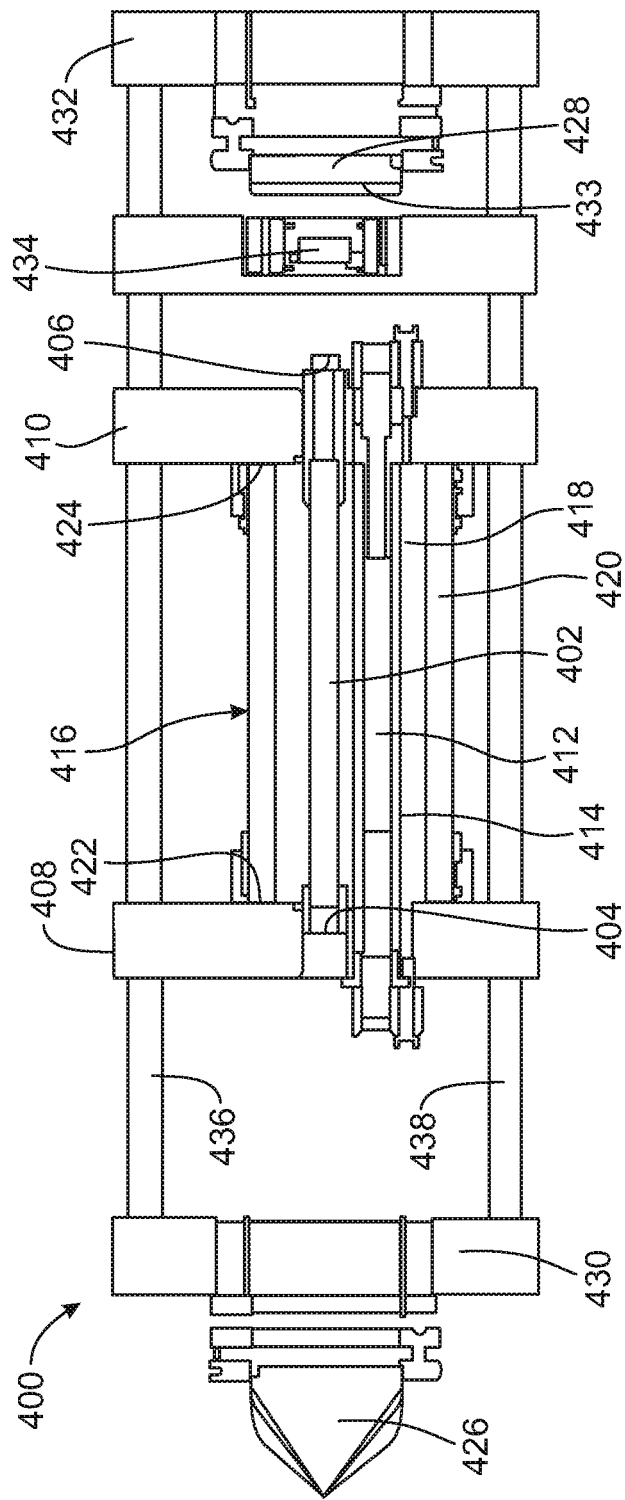
FIG. 4 illustrates various components of another example device that can implement embodiments of the example solid state lasers.

FIG. 4 is a cross-sectional view of another laser 400 disclosed herein. During operation, the laser 400 outputs a laser pulse having a substantially constant pulse energy when the laser 400 is exposed to temperatures between about room temperature and about 200° C., and, thus, the pulse energy is substantially independent of the temperatures. Also, the laser 400 advantageously outputs the laser pulses even when subjected to shocks (e.g., a 500 g shock) and/or vibrations (e.g., a 0.5 g^2/√Hz vibration). In some examples, the laser 400 of FIG. 4 is employed to provide a light source for a variety of spectroscopy techniques (e.g., Raman spectroscopy, absorption spectroscopy, laser induced breakdown spectroscopy, etc.).

The laser 400 includes a solid state gain medium 402 having a first end 404 and a second end 406. In some examples, the solid state gain medium 402 is rod-shaped. In some examples, the solid state gain medium 402 is alexandrite, Nd:YAG, or any other suitable material. The solid state gain medium 402 is held by mounts 408 and 410 at each of the first and second ends 404 and 406 of the solid state gain medium 402. In some examples, the mounts 408 and 410 include apertures (not shown) and/or the solid state gain medium 402 is positioned on the mounts 408 and 410 such that the mounts 408 and 410 are not in the path of the laser pulse during operation.

In the illustrated example, a pump source 412 such as, for example, a flash lamp or an arc lamp is adjacent the solid state gain medium 402. In some examples, the pump source 412 includes a substantially transparent tube 414 (e.g., glass, quartz, etc.) filled with a gas (e.g., Xenon, krypton, etc.). In other examples, the pump source is an LED, a diode laser, and/or any other suitable pump source. The pump source 412 is coupled to an electrical power source (e.g., a capacitor) (not shown). The pump source 412 is also coupled to the mounts 408 and 410 such that longitudinal axes of the pump source 412 and the solid state gain medium 402 are substantially parallel.

A reflective cavity 416 is coupled to the mounts 408 and 410 to substantially enclose the solid state gain medium 402 and the pump source 412. The example reflective cavity 416 illustrated in FIG. 4 includes a substantially transparent (e.g., glass) cylinder 418 at least partially covered by a diffuse reflector 420 such as, for example, barium sulfate, Teflon, and/or any other suitable diffuse reflector. In other examples, the reflective cavity 416 is an elliptical mirror. A first end 422 and a second end 424 of the reflective cavity 416 are at least partially transparent and/or include apertures to enable light to travel out of the reflective cavity 416 and toward a reflective prism 426 and a reflector 428.

In the illustrated example, the reflective prism 426 is adjacent the first end 404 of the solid state gain medium 402. In some examples, the reflective prism 426 is retro-reflective. The example reflective prism 426 of FIG. 4 is coupled to a mount 430 such as, for example, a flexure mount. The reflector 428 is adjacent the second end 406 of the solid state gain medium 402. At least a portion of the example reflector 428 is less than 100 percent reflective to enable the laser pulse to pass through the reflector 428 during operation. In some examples, a reflectivity of the reflector 428 is between about 80 percent and about 90 percent. In the illustrated example, the reflector 428 is coupled to a mount 432 such as, for example, a flexure mount. In some examples, the reflector 428 is curved. The reflective prism 426 and the reflector 428 are substantially aligned such that, during operation, the reflective prism 426 and the reflector 428 provide an optical resonator.

In some examples, the laser 400 does not include the reflective prism 426. In some such examples, a reflector such as, for example, a curved mirror is adjacent the first end 404 of the solid state gain medium 402. In some examples, the reflector 428 is a reflective prism. In some such examples, the laser 400 includes another reflector (not shown) disposed along a path of the laser pulse.

The laser 400 of FIG. 4 includes an optical filter 433 integrated into the reflector 428. In other examples, the optical filter 433 is disposed along the path of the laser pulse and coupled to another mount (not shown) such as, for example, a flexure mount. In such examples, the optical filter 433 is disposed between the reflective prism 426 and the first end 404 of the solid state gain medium 402, between the second end 406 of the solid state gain medium 402 and the reflector 428, or at any other suitable position along the path of the laser pulse. The optical filter 433 may be a birefringent tuner, a Lyot filter, an etalon filter, and/or any other suitable filter to control an output wavelength of the laser pulse outputted by the laser 400. For example, the optical filter 433 enables a wavelength of a laser pulse outputted from the laser 400 having an alexandrite solid state gain medium 402 to be tuned between about 700 nm and about 820 nm.

The laser 400 depicted in FIG. 4 includes a Q-switch 434. In the illustrated example, the Q-switch 434 is a passive Q-switch such as, for example, a saturable absorber. In some examples, the Q-switch 434 is an active Q-switch such as, for example, a rotatable reflector or an electro-optic modulator. The example Q-switch 434 of FIG. 4 is disposed between the second end 406 of the solid state gain medium 402 and the reflector 428 along the path of the laser pulse. In some examples, the Q-switch is coupled (e.g., diffusion bonded, optical contact bonded, etc.) to the solid state gain medium 402.

The mounts 408, 410, 428 and 432 are coupled to braces 436 and 438. In some examples, the laser 400 is disposed in a housing (not shown) in a downhole tool such as, for example, the downhole tool of FIG. 1, the downhole tool of FIG. 2, or any other suitable downhole tool. In some examples, the laser 400 is employed at or near a surface of earth (e.g., in a laboratory).

Figure 5:
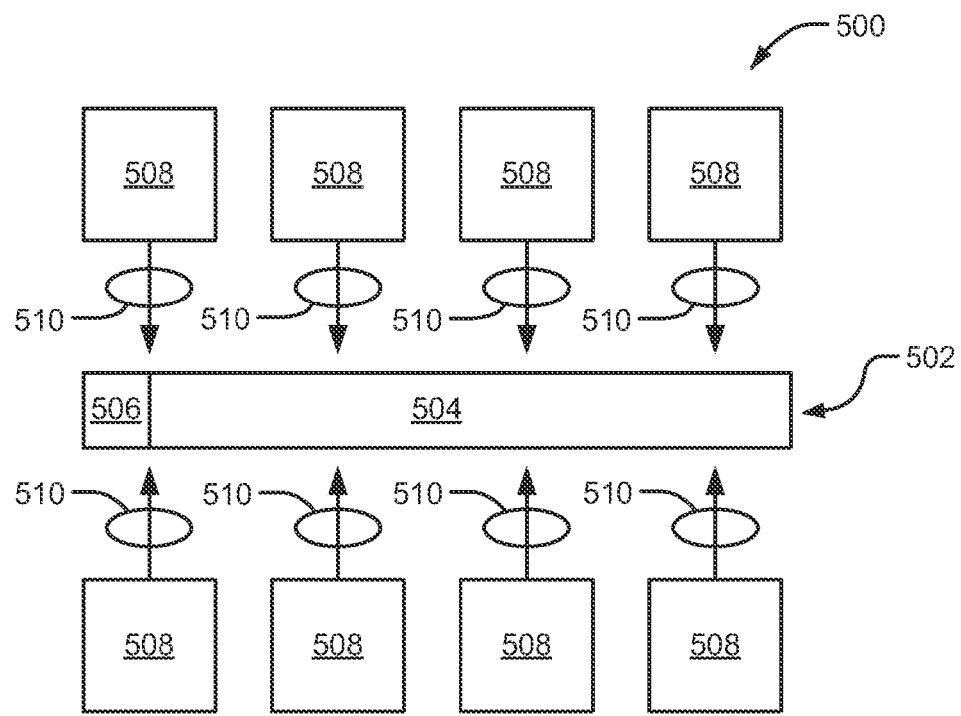
FIG. 5 illustrates various components of another example device that can implement embodiments of the example solid state lasers.

FIG. 5 is a side view of another laser 500 disclosed herein. The laser 500 of FIG. 5 includes a monolithic body 502. The example monolithic body 502 includes a solid state gain medium 504 and a Q-switch 506. In some examples, the monolithic body 502 includes a nonlinear crystal.

In the illustrated example, the solid state gain medium 504 is side-pumped by a plurality of light emitting diodes (LEDs) 508 surrounding the monolithic body 502 to cause a population inversion in the solid state gain medium 504. In some examples, the LEDs 508 emit light corresponding to an absorption peak of the solid state gain medium 504. In the illustrated example, a plurality of collimating and/or focusing optics 510 are disposed between the LEDs 508 and the monolithic body 502 to enhance coupling into the solid state gain medium 504. In other examples, the LEDs 508 and the optics 510 are positioned at an end of the solid state gain medium 504 to emit light along a length of the solid state gain medium 504 and, thus, end-pump the solids state gain medium 504.

Figure 6:
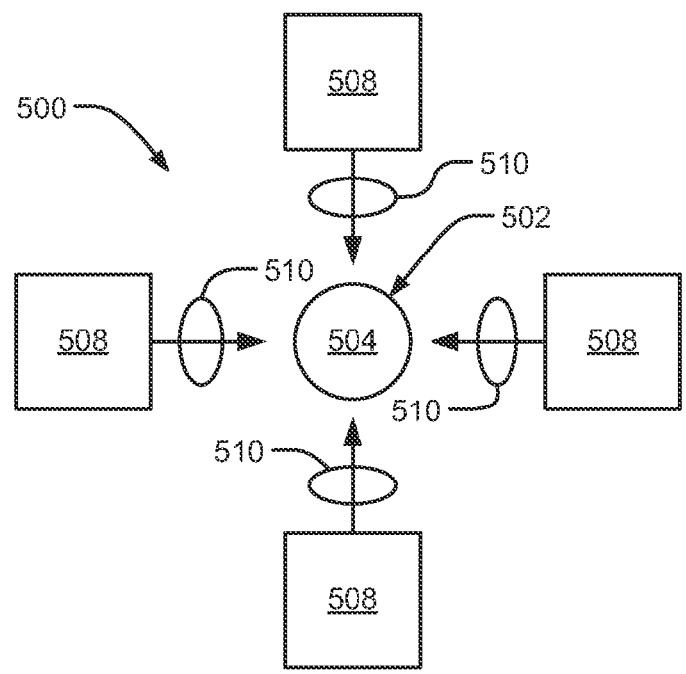
FIG. 6 illustrates various components of the example device of FIG. 5 that can implement embodiments of the example solid state lasers.

FIG. 6 is a rear view of the laser 500 of FIG. 5. In the illustrated example, the LEDs 508 and the optics 510 are disposed adjacent a top, a bottom, a left side and a right side of the example monolithic body 502 in the orientation of FIG. 12. In other examples, the LEDs 508 and the optics 510 are disposed at other positions.

Figure 7:
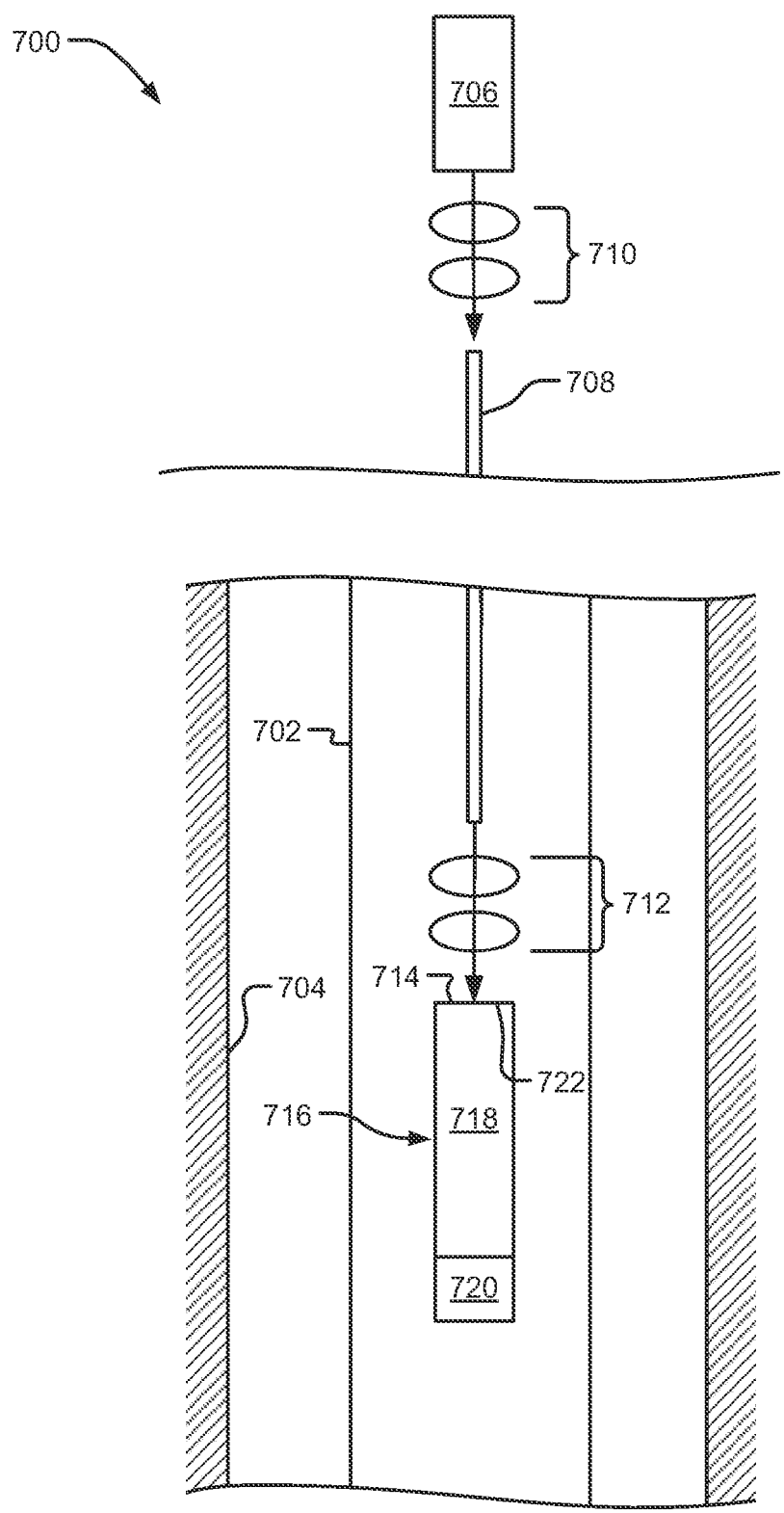
FIG. 7 illustrates various components of another example device that can implement embodiments of the example solid state lasers.

FIG. 7 illustrates another laser 700 disclosed herein. In the illustrated example, a downhole tool 702 (e.g., the example downhole tool of FIG. 1, the example downhole tool of FIG. 2, and/or any other suitable downhole tool) is disposed in a borehole 704, and a diode laser 706 is disposed at or near a surface of Earth. The example diode laser 706 emits light into an optical fiber 708 via first optics 710 (e.g., lenses). In the illustrated example, the optical fiber 708 extends from the surface into the downhole tool 702. The example optical fiber 708 is capable of directing Watts of light into the downhole tool 702.

In the illustrated example, the light emitted via the diode laser 706 travels through the optical fiber 708 and is emitted into the downhole tool 702 toward second optics 712. The example second optics 712 direct the light onto an end 714 of an example monolithic body 716. In the illustrated example, the monolithic body 716 includes a solid state gain medium 718 (e.g., Nd:YAG) and a Q-switch 720. In some examples, the second optics 712 match a mode of the light to a lasing mode of the solid state gain medium 718. In some examples, the monolithic body 716 includes a nonlinear crystal. In the illustrated example, a reflector 722 disposed at the end 714 of the monolithic body 716 adjacent the second optics 712 is substantially transparent to the light emitted from the optical fiber 708 while having a reflectivity of about 100 percent (e.g., 95%, 98%, 99%, 99.9%, etc.) to light at a lasing wavelength of the solid state gain medium 718 (e.g., 1064 nm for Nd:YAG). As a result, the light emitting from the diode laser 706 may travel through the reflector 722 to cause a population inversion in the solid state gain medium 718. In the illustrated example, the monolithic body 716 outputs a laser pulse via the Q-switch 720. In some examples, the laser pulse is directed onto a fluid sample (e.g., in a flowline of the downhole tool 702, in the borehole, etc.) to perform one or more spectroscopy techniques.

FIGS. 8-13 are diagrams of example lasers 800, 900, and 1000 disclosed herein, which may be employed to provide light for a variety of spectroscopy techniques utilizing nonlinear wavelength generation such as, for example, optical parametric oscillation, second, third, or fourth harmonic generation, etc. In some examples, the laser 800, 900, and 1000 may be used to generate supercontinuum light.

Figure 8:
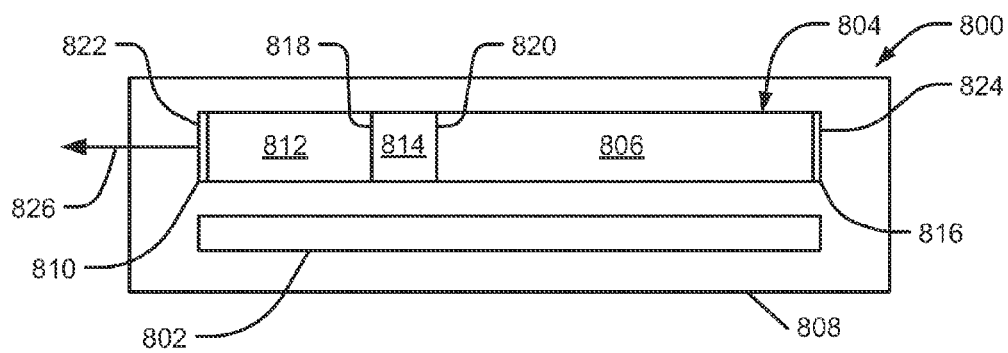
FIG. 8 illustrates various components of another example device that can implement embodiments of the example solid state lasers.

The laser 800 of FIG. 8 includes a pump source 802 such as, for example, a flash lamp, an arc lamp, an LED, a laser diode, and/or any other suitable pump source. The example pump source 802 is adjacent a monolithic body 804 to transversely pump a solid state gain medium 806 of the monolithic body 804. In the illustrated example, a reflective cavity 808 substantially encloses the monolithic body 804 and the pump source 802. In some examples, the reflective cavity 808 is defined by a substantially transparent (e.g., glass) cylinder at least partially covered by a diffuse reflector such as, for example, barium sulfate, Teflon, and/or any other suitable diffuse reflector. In other examples, the reflective cavity 808 is an elliptical mirror.

The example monolithic body 804 of FIG. 8 includes a first reflector 810, a nonlinear crystal 812, a Q-switch 814, the solid state gain medium 806, and a second reflector 816. In the illustrated example, a first end 818 of the Q-switch 814 is coupled to the nonlinear crystal 812, and a second end 820 of the Q-switch 814 is coupled to the solid state gain medium 806. In the illustrated example, the first reflector 810 is disposed on a first end 822 of the monolithic body 804 and the second reflector 816 is disposed on a second end 824 of the monolithic body 804. The example first reflector 810 is coupled to the nonlinear crystal 812, and the example second reflector 816 is coupled to the solid state gain medium 806. In some examples, the first reflector 810 and/or the second reflector 816 are film coatings.

In the illustrated example, the first reflector 810 and the second reflector 816 provide an optical resonator (i.e., reflect light in a closed path). In some examples, reflective surfaces of the first reflector 810 and the second reflector 816 are substantially parallel to each other. In other examples, the first reflector 810 and the second reflector 816 are curved. In some such examples, the first reflector 810 and the second reflector 816 are curved such that the first reflector 810 and the second reflector 816 are substantially confocal or substantially concentric.

The solid state gain medium 806 is a material in a solid state such as, for example, a chromium doped beryllium aluminum oxide crystal ($Cr^{3+}:BeAl_2O_4$) ("alexandrite"), a neodymium-doped yttrium aluminum garnet crystal (Nd:$Y_3Al_5O_{12}$) ("Nd:YAG"), or any other suitable material. In some examples, the solid state gain medium 806 includes a dopant element such as Nd, Yb, Er, Ti, Tm, and/or any other suitable dopant element.

The nonlinear crystal 812 may be composed of Lithium triborate (LBO), potassium titanyl phosphate (KTP), beta-barium borate (BBO), lithium niobate (LN) and/or any other suitable material. In some examples, the nonlinear crystal 812 is a periodically poled material such as, for example, periodically poled lithium niobate (PPLN).

During operation of the laser 800, the pump source 802 causes a population inversion in the solid state gain medium 806, and the nonlinear crystal 812 converts light produced via the solid state gain medium 806 to light having a wavelength different than the light produced via the solid state gain medium 806. For example, if the solid state gain medium 806 is Nd:YAG, the solid state gain medium 806 produces light having a wavelength of 1064 nm, which the nonlinear crystal 812 converts to light having a wavelength such as, for example, 532 nm, 354 nm, or 266 nm.

In the illustrated example, one of the first reflector 810 or the second reflector 816 is anisotropic. The example first reflector 810 and the example second reflector 816 are about 100 percent (e.g., 95%, 98%, 99%, 99.9%, etc.) reflective to the light emitted by the solid state gain medium 806 (e.g., 1064 nm for Nd:YAG). However, the example second reflector 816 has a reflectivity of about 100 percent (e.g., 95%, 98%, 99%, 99.9%, etc.) to the light produced via the nonlinear crystal 812 while the example first reflector 810 has a reflectivity of less than 100 percent (e.g., 80%, 90%, etc.) to the light produced via the nonlinear crystal 812. Thus, the light produced via the solid state gain medium 806 is substantially reflected between the first reflector 810 and the second reflector 816 (i.e., contained in the optical resonator) while the light produced by the nonlinear crystal 812 (i.e., wavelength shifted light) is outputted via the first reflector 810. As a result, the laser 800 outputs a laser pulse 826 having a wavelength of the light produced by the nonlinear crystal 812.

Figure 9:
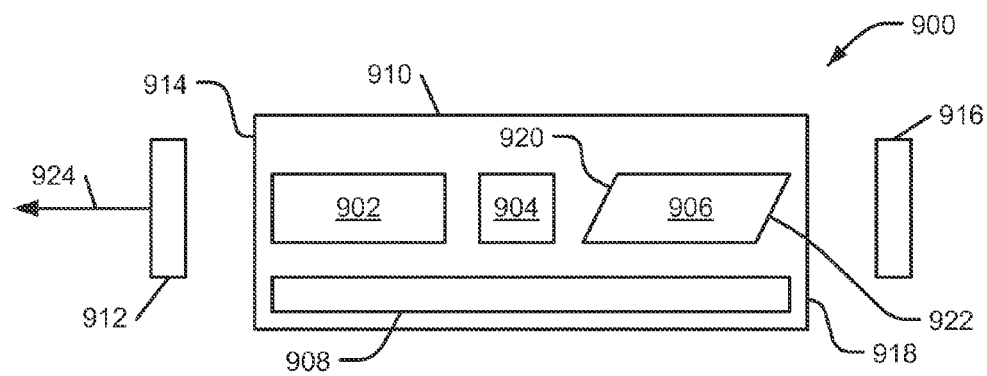
FIG. 9 illustrates various components of another example device that can implement embodiments of the example solid state lasers.

The laser 900 of FIG. 9 includes a nonlinear crystal 902, a Q-switch 904 and a solid state gain medium 906. In the illustrated example, the nonlinear crystal 902, the Q-switch 904 and the solid state gain medium 906 are structurally discrete. In the illustrated example, a pump source 908 (e.g., a flash lamp, an arc lamp, an LED, a laser diode, and/or any other suitable pump source) is disposed adjacent the solid state gain medium 906 to transversely pump the solid state gain medium 906.

In the illustrated example, a reflective cavity 910 substantially encloses the nonlinear crystal 902, the Q-switch 904, the solid state gain medium 906 and the pump source 908. In some examples, the reflective cavity 910 may be defined by a substantially transparent (e.g., glass) cylinder at least partially covered by a diffuse reflector such as, for example, barium sulfate, Teflon, and/or any other suitable diffuse reflector. In other examples, the reflective cavity 910 is an elliptical mirror.

In the illustrated example, a first reflector 912 is disposed adjacent a first end 914 of the reflective cavity 910 and a second reflector 916 is disposed adjacent a second end 918 of the reflective cavity 910. The first reflector 912 and the second reflector 916 provide an optical resonator (i.e., reflect light in a closed path). In some examples, reflective surfaces of the first reflector 912 and the second reflector 916 are substantially parallel to each other. In other examples, the first reflector 912 and the second reflector 916 are curved. In some such examples, the first reflector 912 and the second reflector 916 are curved such that the first reflector 912 and the second reflector 916 are substantially confocal or substantially concentric. In some examples, the first reflector 912 and/or the second reflector 916 is a reflective prism (e.g., a retro-reflective prism).

The example solid state gain medium 906 is a material in a solid state such as, for example, a chromium doped beryllium aluminum oxide crystal ($Cr^{3+}$:$BeAl_2O_4$) ("alexandrite"), a neodymium-doped yttrium aluminum garnet crystal ($Nd$:$Y_3Al_5O_{12}$) ("Nd:YAG"), or any other suitable material. In some examples, the solid state gain medium 906 includes a dopant element such as Nd, Yb, Er, Ti, Tm, and/or any other suitable dopant element. In the illustrated example, a first end 920 and a second end 922 of the solid state gain medium 906 are oriented at a Brewster angle.

The nonlinear crystal 902 may be composed of Lithium triborate (LBO), potassium titanyl phosphate (KTP), beta-barium borate (BBO), lithium niobate (LN) and/or any other suitable material. In some examples, the nonlinear crystal 902 is a periodically poled material such as, for example, periodically poled lithium niobate (PPLN).

During operation of the laser 900, the pump source 908 causes a population inversion in the solid state gain medium 906, and the nonlinear crystal 902 converts light produced via the solid state gain medium 906 to light having a wavelength different than the light produced via the solid state gain medium 906. For example, if the solid state gain medium 906 is Nd:YAG, the solid state gain medium 906 can produce light having a wavelength of 1064 nm, which the nonlinear crystal 902 converts to light having a wavelength such as, for example, 532 nm, 354 nm, or 266 nm.

In the illustrated example, one of the first reflector 912 or the second reflector 916 is anisotropic. The example first reflector 912 and the example second reflector 916 are about 100 percent (e.g., 95%, 98%, 99%, 99.9%, etc.) reflective to the light emitted by the solid state gain medium 906 (e.g., 1064 nm for Nd:YAG). However, the example second reflector 916 has a reflectivity of about 100 percent (e.g., 95%, 98%, 99%, 99.9%, etc.) to the light produced via the nonlinear crystal 902 while the example first reflector 912 has a reflectivity of less than 100 percent (e.g., 80%, 90%, etc.) to light produced via the nonlinear crystal 902. Thus, the light produced via the solid state gain medium 906 is substantially reflected between the first reflector 912 and the second reflector 916 (i.e., contained in the optical resonator) while the light produced by the nonlinear crystal 902 (i.e., wavelength shifted light) is outputted via the first reflector 912. As a result, the laser 900 outputs a laser pulse 924 having a wavelength of the light produced by the nonlinear crystal 902.

Figure 10:
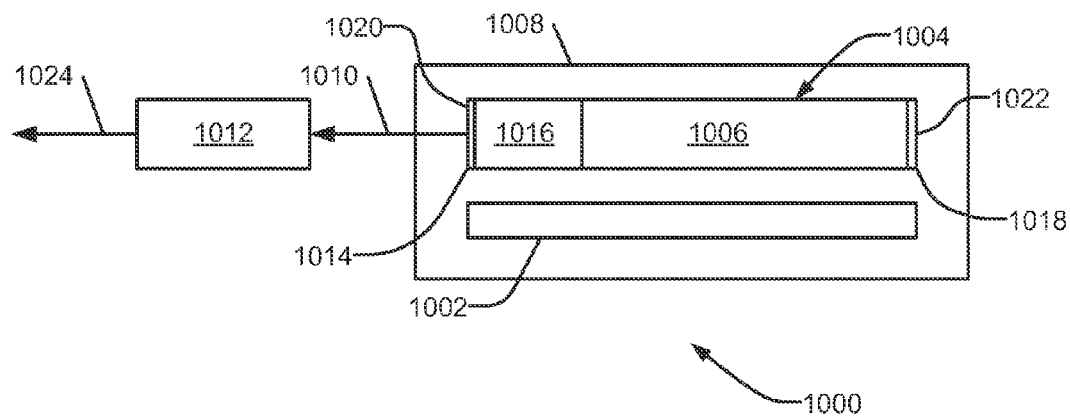
FIG. 10 illustrates various components of another example device that can implement embodiments of the example solid state lasers.

FIG. 10 is a diagram of the laser 1000, which may be used to perform a spectroscopy technique utilizing nonlinear wavelength generation. The laser 1000 of FIG. 10 includes a pump source 1002 such as, for example, a flash lamp, an arc lamp, an LED, a laser diode, and/or any other suitable pump source. The example pump source 1002 is adjacent a monolithic body 1004 to transversely pump a solid state gain medium 1006 of the monolithic body 1004. In the illustrated example, a reflective cavity 1008 substantially encloses the monolithic body 1004 and the pump source 1002. In some examples, the reflective cavity 1008 is defined by a substantially transparent (e.g., glass) cylinder at least partially covered by a diffuse reflector such as, for example, barium sulfate, Teflon, and/or any other suitable diffuse reflector. In other examples, the reflective cavity 1008 is an elliptical mirror. As described in greater detail below, the example monolithic body 1004 outputs a first laser pulse 1010 toward a nonlinear crystal 1012 disposed outside of the reflective cavity 1008.

The example monolithic body 1004 of FIG. 10 includes a first reflector 1014, a Q-switch 1016, the solid state gain medium 1006, and a second reflector 1018. In the illustrated example, the Q-switch 1016 is coupled (e.g., diffusion bonded, optical contact bonded, etc.) to the solid state gain medium 1006. In the illustrated example, the first reflector 1014 is disposed on a first end 1020 of the monolithic body 1004 and the second reflector 1018 is disposed on a second end 1022 of the monolithic body 1004 (e.g., the example first reflector 1014 is coupled to Q-switch 1016, and the example second reflector 1018 is coupled to the solid state gain medium 1006). In some examples, the first reflector 1014 and/or the second reflector 1018 are film coatings.

The solid state gain medium 1006 is a material in a solid state such as, for example, a chromium doped beryllium aluminum oxide crystal ($Cr^{3+}$:$BeAl_2O_4$) ("alexandrite"), a neodymium-doped yttrium aluminum garnet crystal (Nd:$Y_3Al_5O_{12}$) ("Nd:YAG"), or any other suitable material. In some examples, the solid state gain medium 1006 includes a dopant element such as Nd, Yb, Er, Ti, Tm, and/or any other suitable dopant element.

The first reflector 1014 and the second reflector 1018 provide an optical resonator (i.e., reflect light in a closed path). In some examples, reflective surfaces of the first reflector 1014 and the second reflector 1018 are substantially parallel to each other. In other examples, the first reflector 1014 and the second reflector 1018 are curved. In such examples, the first reflector 1014 and the second reflector 1018 are curved such that the first reflector 1014 and the second reflector 1018 are substantially confocal or substantially concentric.

The example second reflector 1018 is about 100 percent (e.g., 95%, 98%, 99%, 99.9%, etc.) reflective to light emitted by the solid state gain medium 1006 (e.g., 1064 nm for Nd:YAG). In some such examples, the first reflector 1014 has a reflectivity of less than 100 percent (e.g., 80%, 90%, etc.) to the light produced via the solid state gain medium 1006 to enable the monolithic body 1004 to output the first laser pulse 1010 (e.g., light) toward the nonlinear crystal 1012 via the first reflector 1014.

In the illustrated example, the nonlinear crystal 1012 is disposed outside of the reflective cavity 1008. The nonlinear crystal 1012 may be composed of Lithium triborate (LBO), potassium titanyl phosphate (KTP), beta-barium borate (BBO), lithium niobate (LN) and/or any other suitable material. In some examples, the nonlinear crystal 1012 is a periodically poled material such as, for example, periodically poled lithium niobate (PPLN).

During operation of the laser 1000, the pump source 1002 causes a population inversion in the solid state gain medium 1006 and the monolithic body 1004 outputs the first laser pulse 1010 toward the nonlinear crystal 1012. As the first laser pulse 1010 passes through the nonlinear crystal 1012, the nonlinear crystal 1012 converts the first laser pulse 1010 to a second laser pulse 1024 having a wavelength different than the first laser pulse 1010. For example, if the solid state gain medium 1006 is Nd:YAG, the solid state gain medium 1006 produces the first laser pulse 1010 having a wavelength of 1064 nm, which the nonlinear crystal 1012 converts to the second laser pulse 1024 having a wavelength such as, for example, 532 nm, 354 nm, or 266 nm.

Figure 11:
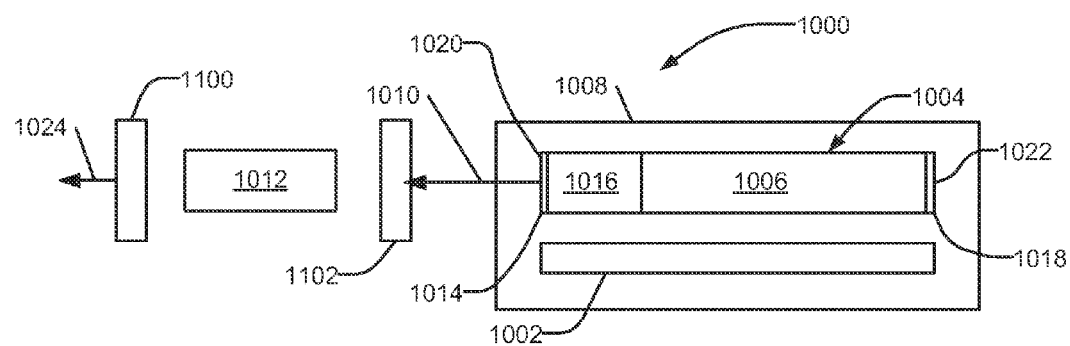
FIG. 11 illustrates various components of the example device of FIG. 10 that can implement embodiments of the example solid state lasers.

FIG. 11 is a diagram of the laser 1000 in which the nonlinear crystal 1012 is disposed between a third reflector 1100 and a fourth reflector 1102. In the illustrated example, the third reflector 1100, the nonlinear crystal 1012, and the fourth reflector 1102 are disposed outside of the reflective cavity 1008 along a path of the first laser pulse 1010.

In the illustrated example, the third reflector 1100 and the fourth reflector 1102 reflect a fundamental wavelength of the first laser pulse 1010. As a result, the first laser pulse 1010 passes through the fourth reflector 1102, and the nonlinear crystal 1012 converts the first laser pulse 1010 to light having a wavelength different than the first laser pulse 1010. In the illustrated example, the third reflector 1100 and the fourth reflector 1102 provide an optical resonator for the light produced via the nonlinear crystal 1012, and the laser 1000 outputs the second laser pulse 1024 via the third reflector 1100. Thus, the second laser pulse 1024, which has a wavelength of the light produced via the nonlinear crystal 1012, is outputted via the third reflector 1100.

Figure 12:
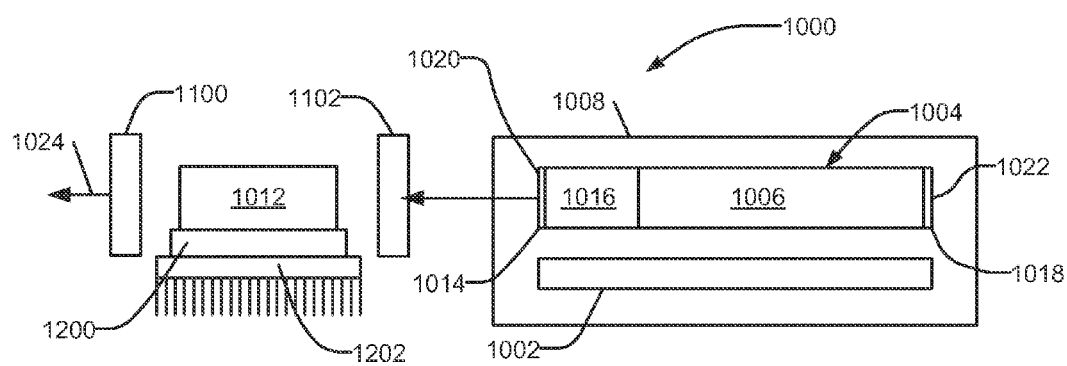
FIG. 12 illustrates various components of the example device of FIG. 10 that can implement embodiments of the example solid state lasers.

FIG. 12 illustrates the laser 1000 of FIG. 11 in which the nonlinear crystal 1012 is coupled to a heat pump 1200 (e.g., a Peltier thermoelectric device) and a heat sink 1202 to control a temperature of the nonlinear crystal 1012 to achieve noncritical phase matching. For example, noncritical phase matching may occur for second harmonic generation of light having a wavelength of 1064 nm by adjusting a temperature of a lithium triborate (LBO) crystal to 148° C.

Figure 13:
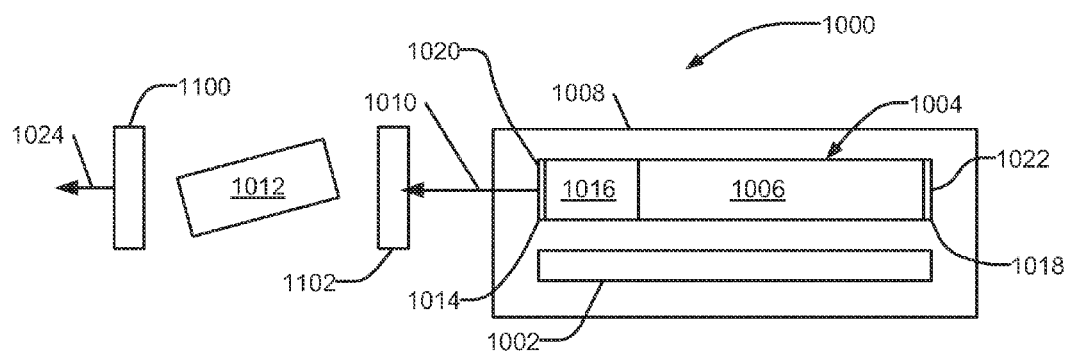
FIG. 13 illustrates various components of the example device of FIG. 10 that can implement embodiments of the example solid state lasers.

FIG. 13 illustrates the laser 1000 of FIG. 11 in which a longitudinal axis of the nonlinear crystal 1012 is nonparallel to an optical axis of the pump source 1002. In the illustrated example, the nonlinear crystal 1012 is oriented such that noncritical phase matching may be achieved.

Figure 14:
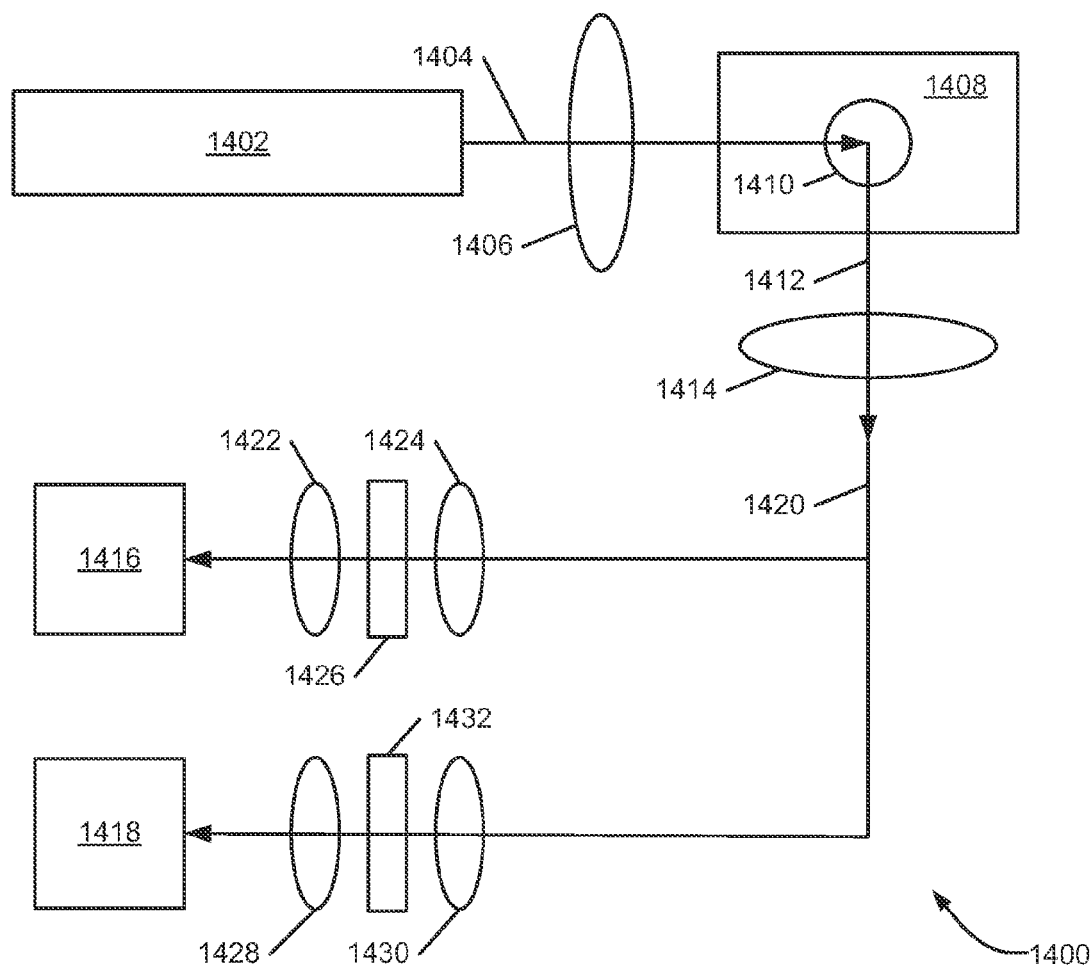
FIG. 14 illustrates another example system in which embodiments of the example solid state lasers can be implemented.

FIG. 14 is a diagram of an example system 1400, which may be used to perform laser induced breakdown spectroscopy (LIBS) to, for example, determine an elemental concentration of a fluid and/or identify constituent molecules of the fluid.

The example system 1400 includes a solid state laser 1402. The solid state laser 1402 may be implemented using, for example, the laser 300 of FIG. 3, the laser 400 of FIG. 4, the laser 500 of FIGS. 5-6, the example lasers 700 of FIG. 7, and/or one of the example lasers 800, 900, 1000, or 1100 of FIGS. 8-13. In the illustrated example, a laser pulse 1404 outputted via the solid state laser 1402 is focused via focusing optics 1406 onto a fluid sample 1408 (e.g., liquid(s) and/or gas(es) in a flowline of a downhole tool, fluid in a borehole, etc.). As a result, a portion of the fluid sample 1408 is ionized such that plasma 1410 including ion cores and free electrons are formed.

In the illustrated example, light 1412 emitted from the plasma 1410 is collected via collection optics 1414 and directed to a first detector 1416 and a second detector 1418 via a fiber optic bundle 1420. Other examples include other numbers of detectors (e.g., 1, 3, 4, 5, etc.). In the illustrated example, the first detector 1416 includes a first pair of collimating and focusing optics 1422 and 1424 and a first bandpass optical filter 1426. The example second detector 1418 includes a second pair of collimating and focusing optics 1428 and 1430 and a second bandpass optical filter 1432. In some examples, the first detector 1416 and/or the second detector 1418 is a spectrometer including a plurality of wavelength channels (e.g., an echelle grating based spectrometer) and/or a monochromator. Based on the light 1412 emitted from the plasma 1410, the first detector 1416 and/or the second detector 1418 determine a characteristic of the fluid sample 1408 (e.g., elemental concentrations, concentration of tracer elements, etc.).

Figure 15:
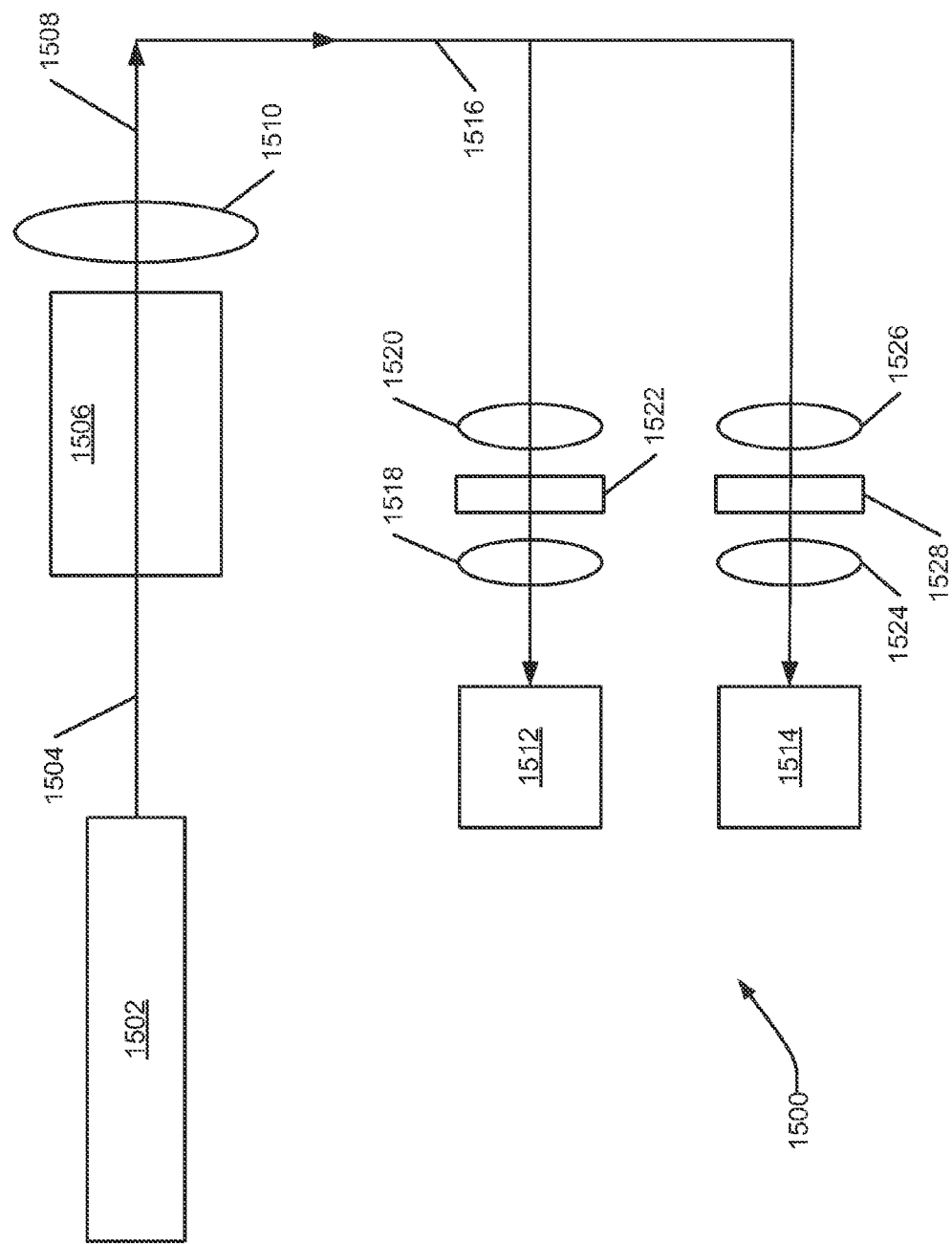
FIG. 15 illustrates another example system in which embodiments of the example solid state lasers can be implemented.

FIG. 15 is a diagram of an example system 1500, which may be used to perform absorption spectroscopy. Absorption spectroscopy may be performed to determine a concentration of constituent molecules (e.g., saturated compounds such as, for example, methane or ethane) of a fluid.

The example system 1500 includes a solid state laser 1502, which may be implemented using, for example, one of the example lasers 800, 900, and 1000 of FIGS. 8-13. In the illustrated example, light 1504 emitted by the example solid state laser 1502 is directed onto a fluid sample 1506 (e.g., fluid flowing through a flowline, fluid disposed in a borehole, etc.). Light 1508 emitted by the fluid sample (i.e., light that passes through the fluid sample) is collected via collection optics 1510 and directed to a first detector 1512 and a second detector 1514 via a fiber optic bundle 1516.

In the illustrated example, the first detector 1512 includes a first pair of collimating and focusing optics 1518 and 1520 and a first bandpass optical filter 1522. The example second detector 1514 includes a second pair of collimating and focusing optics 1524 and 1526 and a second bandpass optical filter 1528. In some examples, the first detector 1512 and/or the second detector 1514 includes a spectrometer including a plurality of wavelength channels (e.g., an echelle grating based spectrometer). Based on the light 1508 emitted by (i.e., passing through) the fluid sample 1506, a characteristic of the fluid sample 1506 may be determine via the first detector 1512 and/or the second detector 1514.

FIGS. 16, 17, 18 and 19 illustrate example spectroscopy systems 1600, 1700, 1800 and 1900 which may be used to perform Raman spectroscopy (e.g., a Raman spectrometer) for sample composition analysis, including, for example, the Raman spectroscopy techniques described in U.S. Publication No. 2008/0111064, titled "Downhole Measurement of Substances in Earth Formations," filed Nov. 10, 2006.

Figure 16:
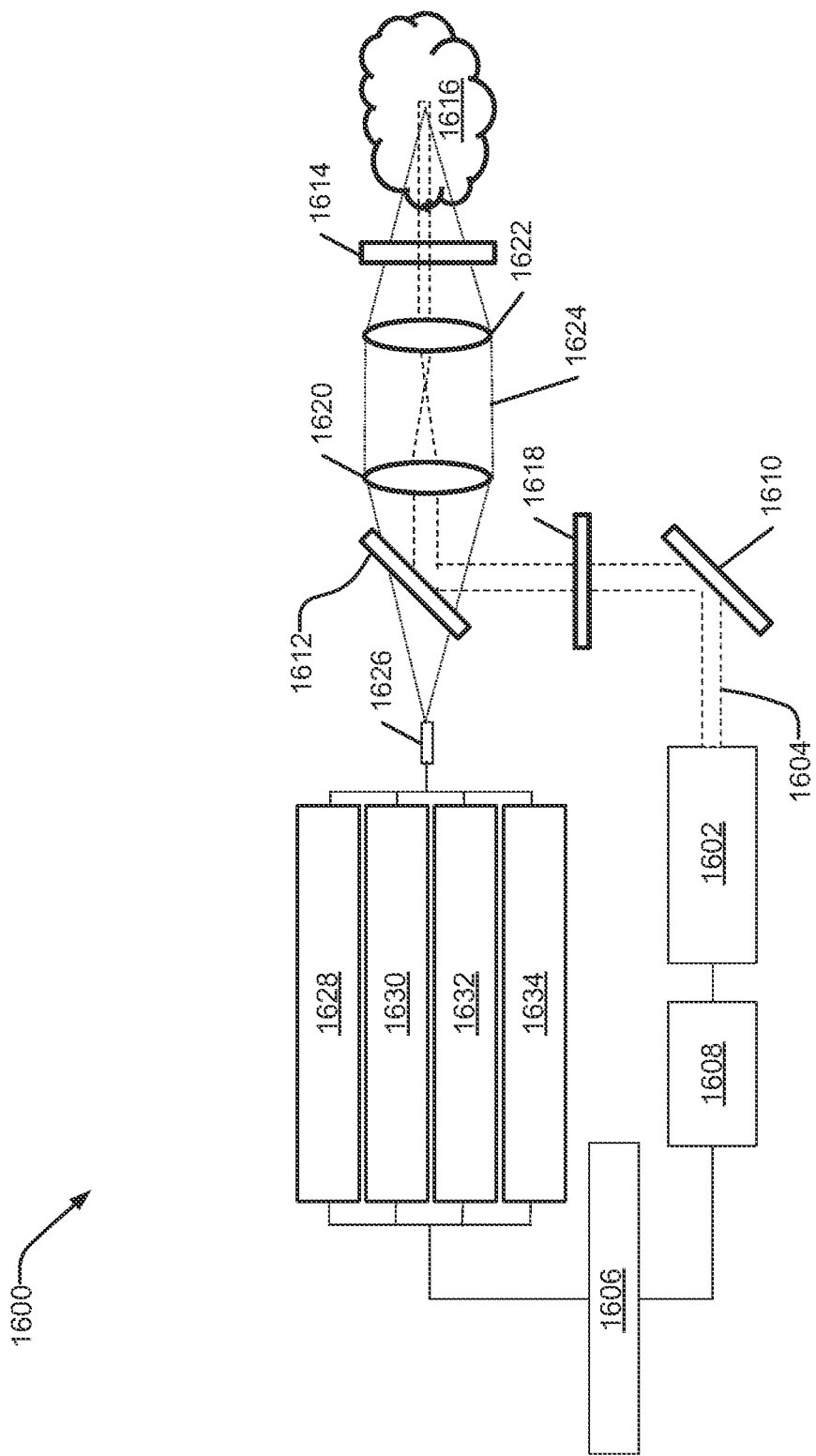
FIG. 16 illustrates another example system in which embodiments of the example solid state lasers can be implemented.

In illustrative embodiments, the spectroscopy system provides collimated excitation light to the sample and collects scattered light from the sample. Such spectroscopy systems use collimated excitation light to avoid high intensity excitation light within the sample and adjacent optics, which prevents damage to the adjacent optics, ionization of the sample, and/or other non-linear interactions between the excitation light and the sample. The example system 1600 of FIG. 16 includes a solid state laser 1602 to emit a first beam 1604 of light. The example solid state laser 1602 of FIG. 16 may be implemented using the laser 300, 400, 500, 600, 700 and/or any other suitable solid state laser. In the illustrated example, the solid state laser 1602 is coupled to a controller 1606 (e.g., a microprocessor) via a high voltage or pulse forming network 1608. In the illustrated example of FIG. 16, the first beam 1604 (e.g., excitation light) is directed via a mirror 1610 and a first filter 1612 (e.g., a dichroic filter) through a window 1614 (e.g., a sapphire window) onto a sample 1616 (e.g., a solid, liquid and/or gas). In the illustrated example, the first beam 1604 passes through a second filter 1618 disposed between the mirror 1610 and the first filter 1612. A first lens 1620 and a second lens 1622, disposed between the first filter 1612 and the window 1614, collimate the first beam 1604 and direct the first beam 1604 onto the sample 1616. As explained above, the first beam 1604 strikes the sample 1616 as a collimated beam and, in this manner, prevents high intensity excitation light within the sample. In some embodiments of the present disclosure, the interrogated sample volume 1616 of FIG. 16 is located at a specific distance from the window 1614. The distance of the sample volume from the window is controlled by the choice of lens elements 1622 of FIG. 16. It is understood that the present disclosure is not limited to any particular choice of length resulting from different combinations of said lens elements. In the specific illustrated example, the window 1614 is a distance from the sample 1616 substantially equal to the inverse of an absorption coefficient of the sample 1616 at a wavelength of light to be scattered by the sample 1616. In other examples, the window 1614 is other distances from the sample 1616 (e.g., less than three time the inverse of the absorption coefficient).

In the illustrated example, the first beam 1604 interacts with the sample 1616 (e.g., Raman scattering, absorption and/or emissions from a plasma formed by breakdown of a portion of the sample 1616, etc.). A second beam 1624 of light emitted from the sample 1616 (e.g., diverging Raman scattered light) passes through the window 1614 and is focused onto a fiber bundle 1626 via the first lens 1620 and the second lens 1622. In the illustrated example, the second beam 1624 is also directed through the first filter 1612. Via the fiber bundle 1626, the second beam 1624 is directed to a plurality of detectors 1628, 1630, 1632, 1634 (e.g., spectrometers, photodiodes, etc.). In the illustrated examples, each of the plurality of detectors 1628, 1630, 1632, 1634 is coupled to the controller 1606. Based on the second beam 1624 (e.g., an intensity of $CC_v$ and $CH_v$ channels), a characteristic of the sample 1616 (e.g., a composition of gas condensates) may be determined. In some examples, a reduction in collected Raman scattered photons (e.g., due to absorption from one or more constituents of the sample 1616) is determined and/or corrected for by measuring a concentration of the one or more constituents. In some examples, the concentration of the one or more constituents is measured by determining photons scattered by a Raman band of the one or more constituents.

Figure 17:
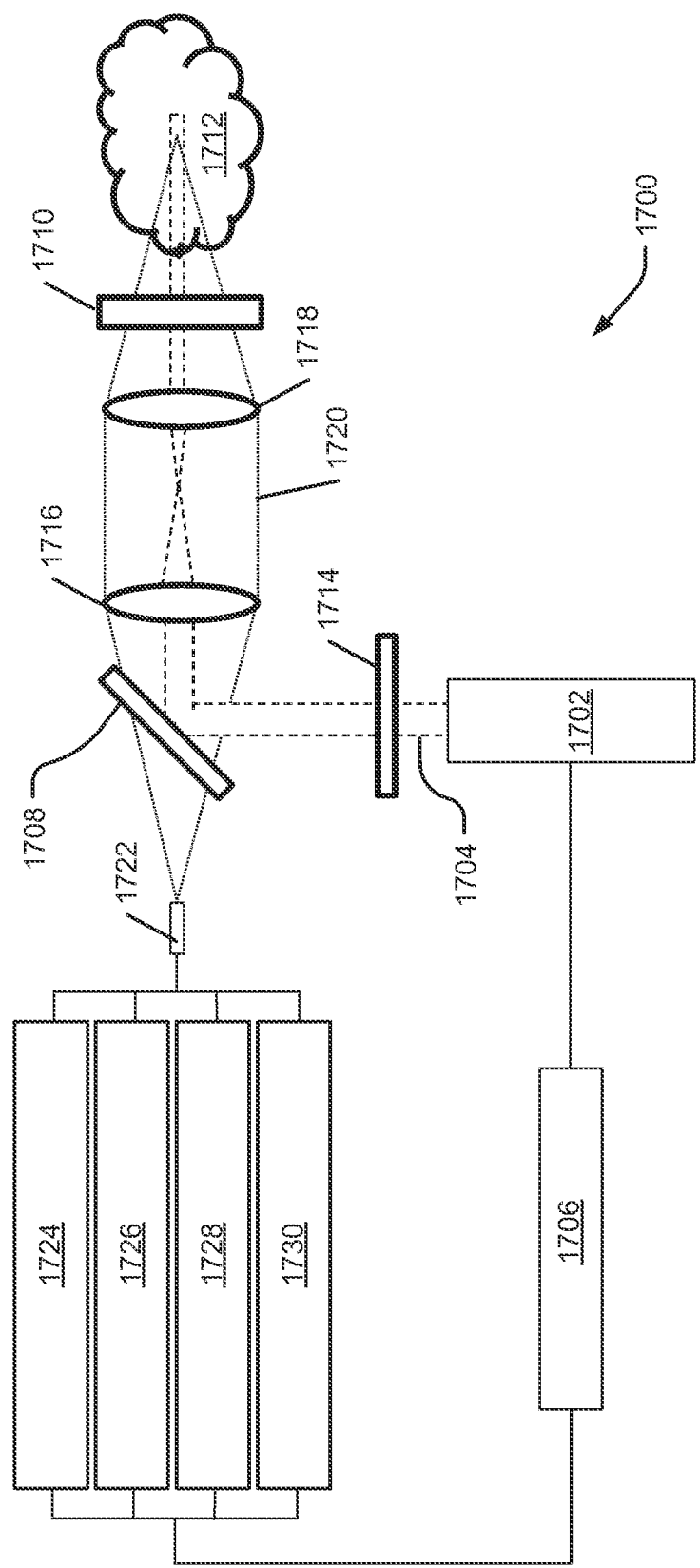
FIG. 17 illustrates another example system in which embodiments of the example solid state lasers can be implemented.

The example system 1700 of FIG. 17 includes a solid state laser 1702 to emit a first beam 1704 of light. The example solid state laser 1702 of FIG. 17 may be implemented using the example lasers 300, 400, 500, 600, 700 and/or any other suitable solid state laser. In the illustrated example, the solid state laser 1702 is coupled to a controller 1706 (e.g., a microprocessor). In the example system 1700 of FIG. 17, the first beam 1704 is directed via a first filter 1708 (e.g., a dichroic filter) through a window 1710 (e.g., a sapphire window) onto a sample 1712 (e.g., a liquid, solid and/or gas). In the illustrated example, the first beam 1704 (e.g., excitation light) passes through a second filter 1714 disposed between the solid state laser 1702 and the first filter 1708. The example system 1700 also includes a plurality of optical members. In this case, a first lens 1716 and a second lens 1718, disposed between the first filter 1708 and the window 1710, collimate the first beam 1704 and direct the first beam 1704 onto the sample 1712. As explained above, the first beam 1704 strikes the sample 1716 as a collimated beam and, in this manner, prevents high intensity excitation light within the sample. In the illustrated example, the window 1710 is a distance from the sample 1712 substantially equal to three times an inverse of an absorption coefficient of the sample 1712 at a wavelength of light to be scattered by the sample 1712. In other examples, the window 1710 is other distances from the sample 1712 (e.g., less than three time the inverse of the absorption coefficient).

In the illustrated example, the first beam 1704 interacts with the sample 1712 (e.g., Raman scattering, absorption and/or emissions from a plasma formed by breakdown of a portion of the sample 1712, etc.). A second beam 1720 of light emitted from the sample 1712 (e.g., diverging Raman scattered light) passes through the window 1710 and is focused onto a fiber bundle 1722 via the first lens 1716 and the second lens 1718. In the illustrated example, the second beam 1720 is also directed through the first filter 1708. Via the fiber bundle 1722, the second beam 1720 is directed to a plurality of detectors 1724, 1726, 1728 and 1730 (e.g., spectrometers, photodiodes, etc.). Based on the second beam 1720 (e.g., an intensity of $CC_v$ and $CH_v$ channels), a characteristic of the sample 1712 (e.g., a composition of gas condensates) may be determined. In some examples, a reduction in collected Raman scattered photons (e.g., due to absorption from one or more constituents of the sample 1712) is determined and/or corrected for by measuring a concentration of the one or more constituents. In some examples, the concentration of the one or more constituents is measured by determining photons scattered by a Raman band of the one or more constituents.

The first lens 1716 and the second lens 1718 may have a variety of different focal lengths, diameters and configurations to provide collimated excitation light to the sample. The present disclosure is not limited to the configurations illustrated in FIG. 16 and FIG. 17.

Figure 18:
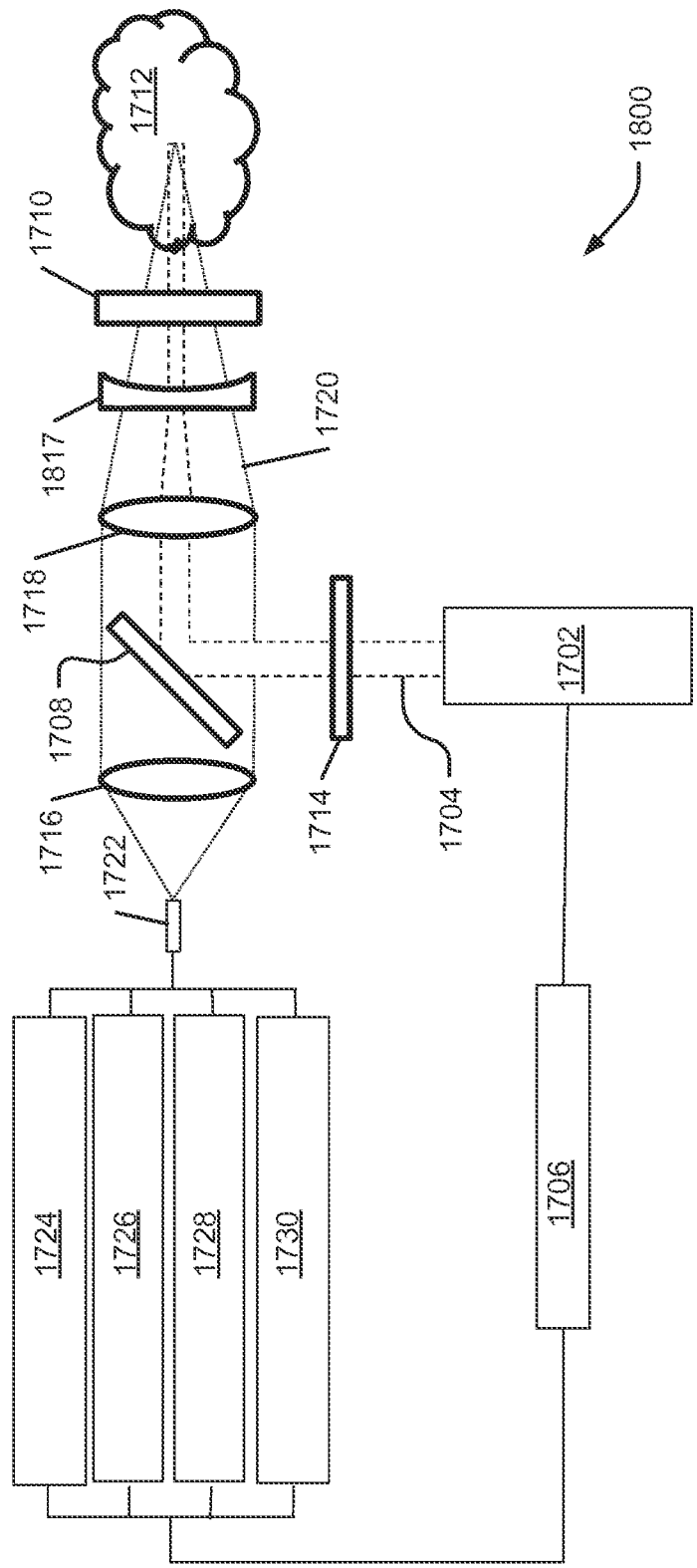
FIG. 18 illustrates yet another example system in which embodiments of the example solid state lasers can be implemented.

In another example, as shown in the system 1800 of FIG. 18, an internal beam waist between the first lens 1716 and the second lens 1718 is eliminated by positioning the first lens 1816 between the fiber 1722 and the dichroic beam splitter 1708 and inserting a third lens element 1817 between the second lens 1718 and the window 1710. In this configuration, the light passing through the dichroic beam splitter 1708 is collimated.

Figure 19:
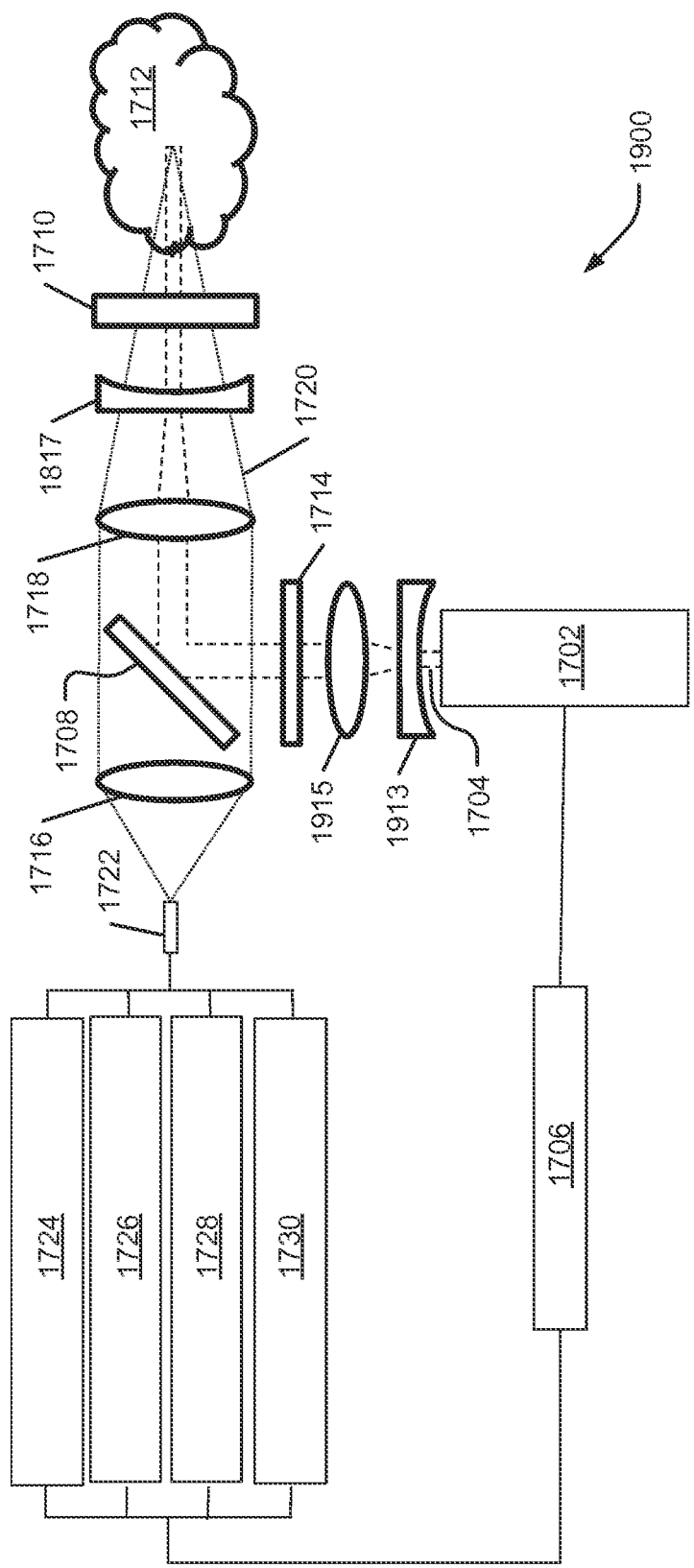
FIG. 19 illustrates a further example system in which embodiments of the example solid state lasers can be implemented.

In yet another example, as shown in the system 1900 of FIG. 19, lens optics are provided to modify the excitation beam diameter (e.g., expand or compress) that is emitted by the laser 1702. In the particular embodiment of FIG. 19, a first lens 1913 and a second lens 1915 are inserted between the dichroic beam splitter 1708 and the laser 1702. Such lens optics may also be incorporated in the system 1600 of FIG. 16, the system 1700 of FIG. 17, or the system 1800 of FIG. 18.

Figure 20:
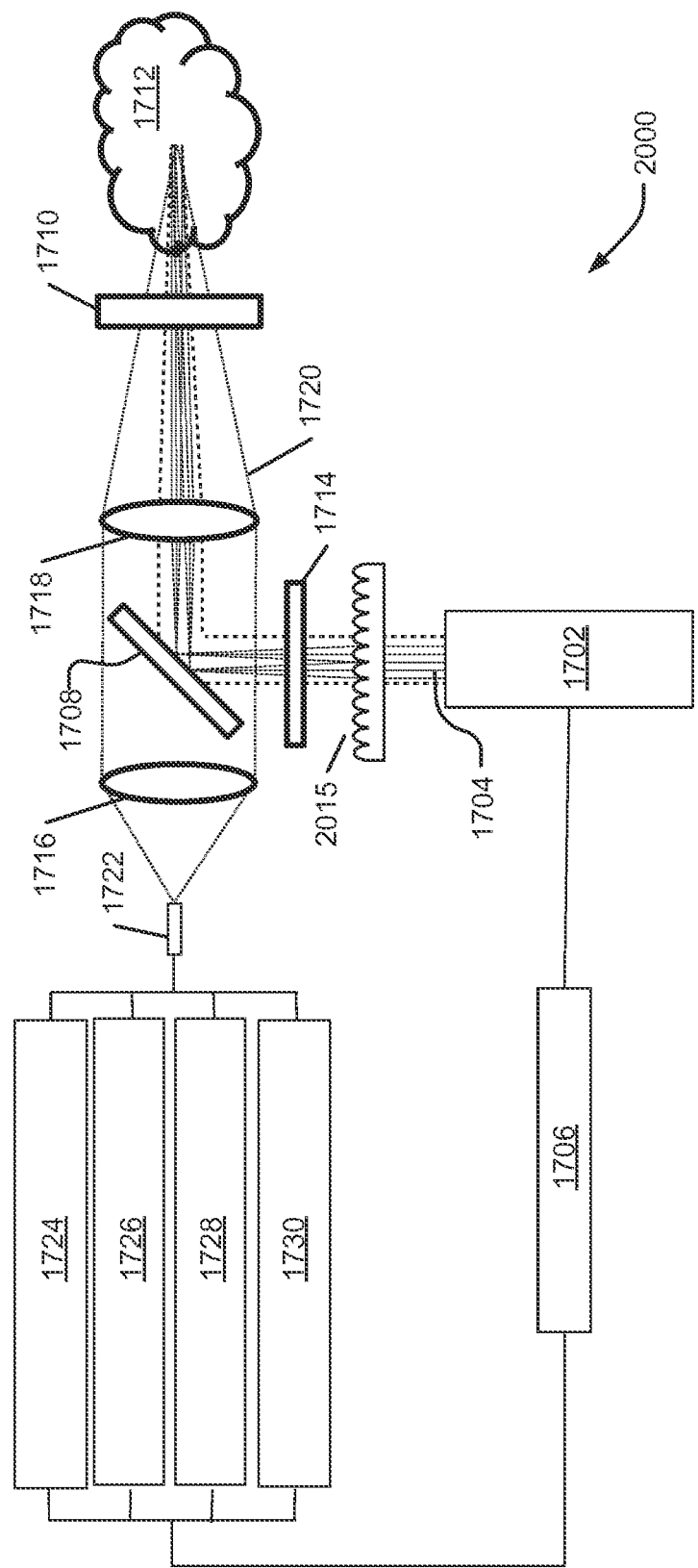
FIG. 20 illustrates another example system in which embodiments of the example solid state lasers can be implemented.
Figure 22:
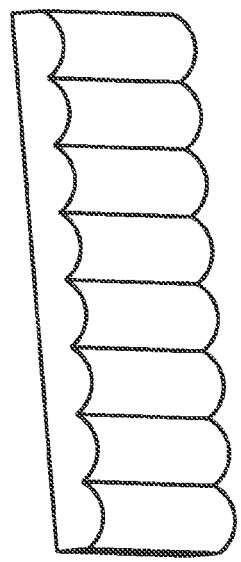
FIG. 22 illustrates an array of cylindrical lenslets in accordance with one embodiment of the present disclosure.
Figure 24:
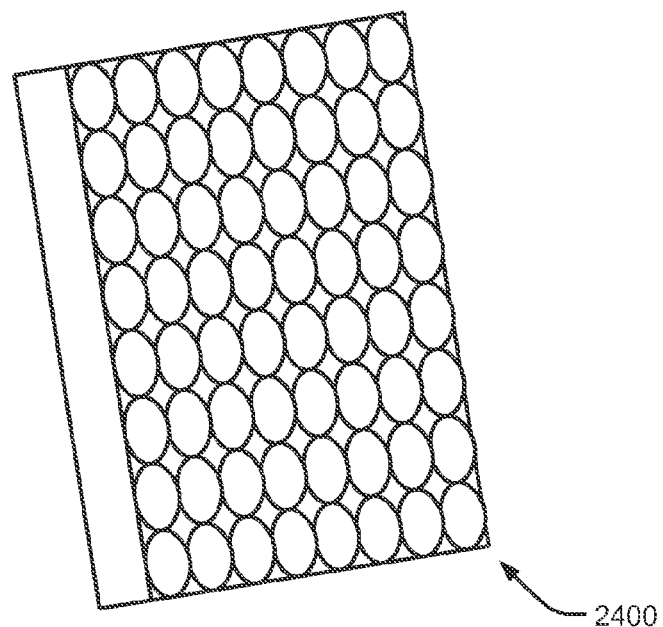
FIG. 24 illustrates an array of spherical lenslets in accordance with one embodiment of the present disclosure.

In yet another example, the system reduces the beam intensity at the window and/or the sample by using a beam homogenizer. In this manner, various embodiments of the system further reduce high intensity excitation light within the sample and adjacent optics, which prevents damage to the adjacent optics, ionization of the sample, and/or other non-linear interactions between the excitation light and the sample. In one embodiment, as shown in the system of FIG. 20, the system 2000 includes a non-imaging beam homogenizer. The non-imaging beam homogenizer includes a micro-lens array 2015 that is inserted between the laser 1702 and the filter 1714. In some embodiments, the micro lens array 2015 comprises an array of spherical lenslets 2400, as shown in FIG. 24, or a pair of crossed arrays of cylindrical lenslets 2200, as shown in FIG. 22. The lenslet array divides the input beam profile into a plurality of slices. A spherical lens 1718 maps the individual beams to the sample focal plane 1712 producing a more uniform intensity profile.

Figure 21:
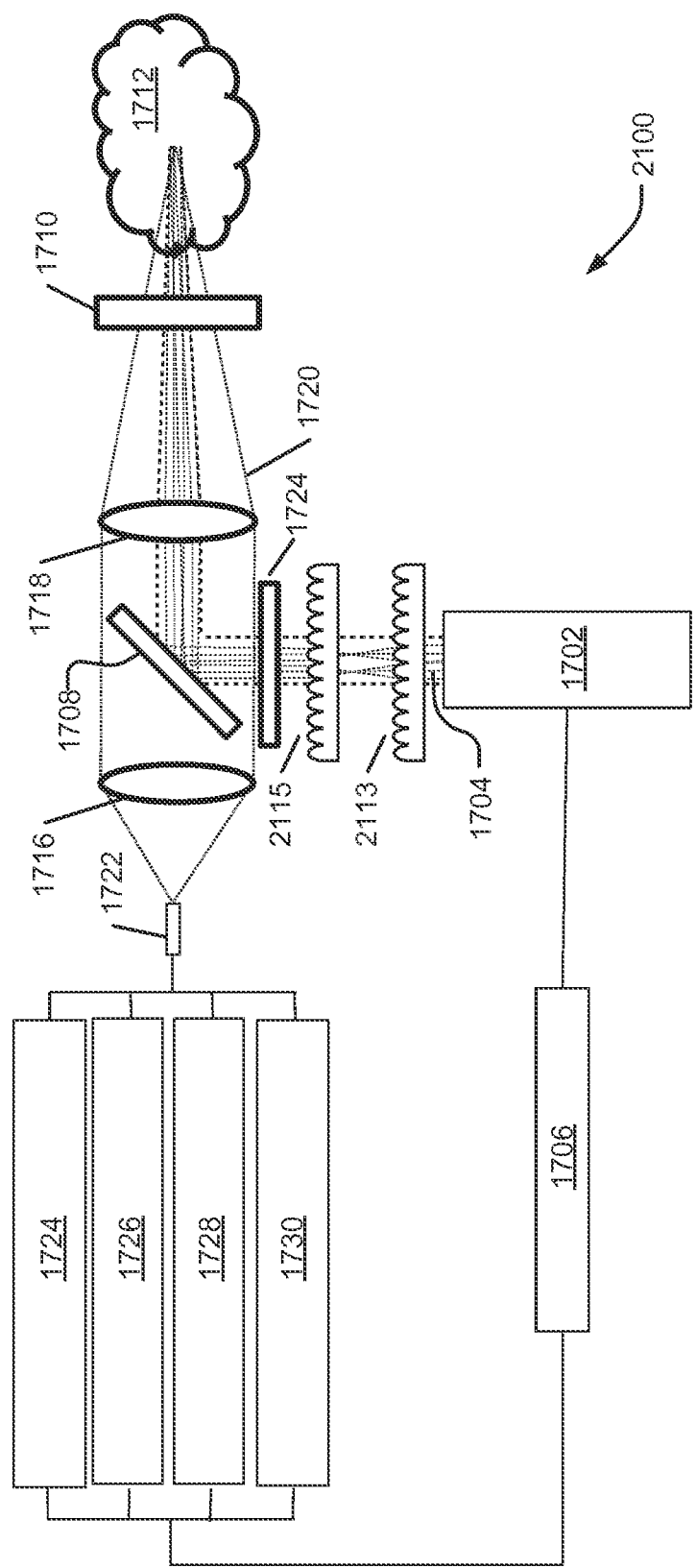
FIG. 21 illustrates a further example system in which embodiments of the example solid state lasers can be implemented.

In yet another example, as shown in the system of FIG. 21, the beam intensity at the window 1710 is reduced by providing an imaging beam homogenizer, which includes a pair of micro-lens arrays 2113 and 2115 that are inserted between the laser 1702 and the filter 1714. In some embodiments, the micro lens arrays comprise an array of spherical lenslets 2400, as shown in FIG. 24, or a pair of crossed arrays of cylindrical lenslets 2200, as shown in FIG. 22. The lenslet array divides the input beam profile into a plurality of slices. A spherical lens 1718 reimages the individual slices to the sample focal plane 1712 producing a more uniform intensity profile.

Figure 23:
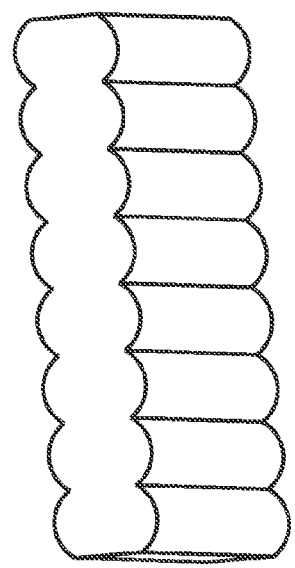
FIG. 23 illustrates a fly's eye condenser array in accordance with one embodiment of the present disclosure.

The present disclosure is not limited to the configurations illustrated in FIG. 20 and FIG. 21. For example, in some embodiments, the micro lens arrays 2113 and 2115 in the system 2100 of FIG. 21 can be combined to form a fly's eye condenser array 2300, as shown in FIG. 23. In another embodiment, the micro lens arrays 2113 and 2115 may be a crossed fly's eye condenser array.

Figure 25:
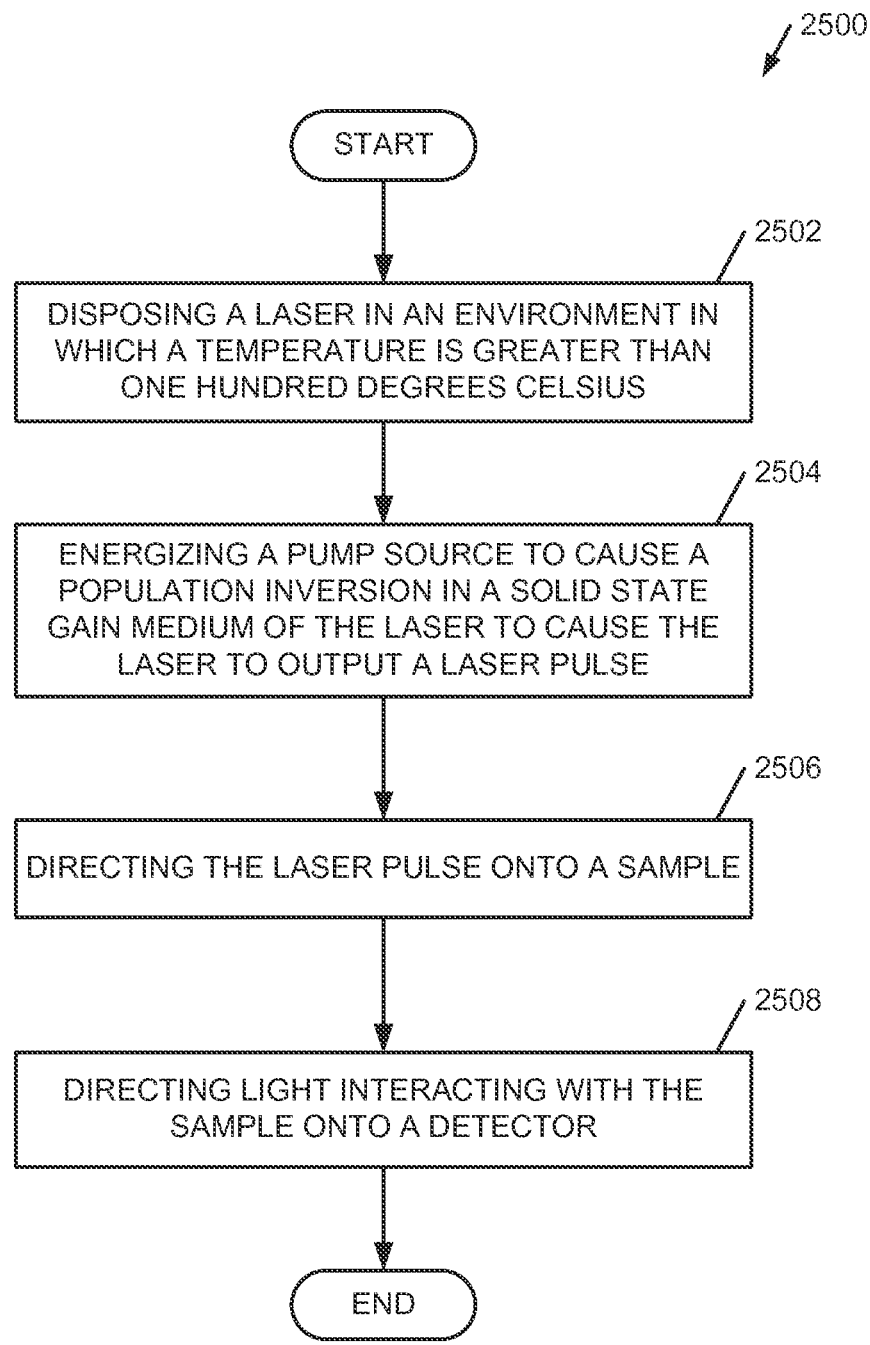
FIG. 25 illustrates example method(s) in accordance with one or more embodiments of the present disclosure.

FIG. 25 depicts an example flow diagram representative of processes that may be implemented using, for example, computer readable instructions. The example process of FIG. 20 may be performed using a processor, a controller and/or any other suitable processing device. For example, the example process of FIG. 25 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. The example process of FIG. 25 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

The example process of FIG. 25 may be implemented using any combination(s) of application specific integrated circuit(s) (ASIC(s)), programmable logic device(s) (PLD(s)), field programmable logic device(s) (FPLD(s)), field programmable gate array(s) (FPGA(s)), discrete logic, hardware, firmware, etc. Also, one or more operations depicted in FIG. 20 may be implemented manually or as any combination(s) of any of the foregoing techniques, for example, any combination of firmware, software, discrete logic and/or hardware. In some examples, the example process of FIG. 20 may be implemented using the logging and control unit of FIG. 1A, the electronics and processing system 166, an uphole processor and/or a downhole control system. Further, one or more operations depicted in FIG. 25 may be implemented at the surface and/or downhole.

Further, although the example process of FIG. 25 is described with reference to the flow diagram of FIG. 25, other methods of implementing the process of FIG. 25 may be employed. For example, the order of execution of the blocks may be changed, and/or some of the blocks described may be changed, omitted, sub-divided, or combined. Additionally, one or more of the operations depicted in FIG. 25 may be performed sequentially and/or in parallel by, for example, separate processing threads, processors, devices, discrete logic, circuits, etc.

FIG. 25 depicts an example process 2500 disclosed herein. The example process 2500 begins by disposing a laser (e.g., the example lasers 300, 400, 500, 700, 800, 900, 1000, the example monolithic body 716, the solid state laser 1402, the solid state laser 1502, etc.) in an environment in which a temperature is greater than 100 degrees Celsius (block 2502). In some examples, the laser includes a monolithic body having a first reflector, a second reflector, and a solid state gain medium disposed between the first reflector and the second reflector. In some examples, the environment is downhole. In some such examples, the laser is disposed in a downhole tool (e.g., the production logging 100, the wireline tool 200, etc.), and the downhole tool is lowered into a borehole.

At block 2504, a pump source (e.g., one or more of the example pump sources 314, 412, 802, 908, 1002, the LEDs 508 of FIG. 5, the diode laser 706 of FIG. 7, etc.) is energized to cause a population inversion in the solid state gain medium of the laser to cause the laser to output a laser pulse. In some examples, a flash lamp, a plurality of LEDs, and/or one or more diode lasers are energized to cause a population inversion in the solid state gain medium. In some examples, light from the pump source is directed onto a fiber optic cable, which directs the light onto the solid state gain medium.

At block 2506, the laser pulse is directed onto a sample. In some examples, the laser pulse is directed onto a sample via collimating optics (e.g., the optics 1620 and 1622 of FIG. 16, the optics 1716 and 1718 of FIG. 17, the optics 1716 and 1718 and 1817 of FIG. 18, the optics 1913 and 1915 of FIG. 19). At block 2508, light interacting with the sample is directed (e.g., collected and focused by the optics 1620 and 1622 of FIG. 16, the optics 1716 and 1718 of FIG. 17, etc., the optics 1816 and 1818 and 1817 of FIG. 18, etc., the optics 1913 and 1915 of FIG. 19, etc.) onto a detector. In some such examples, the detector determines one or more characteristics of the sample based on the light interacting with the sample (e.g., light scattered by constituents of the sample).

Although only a few examples have been described in detail above, those skilled in the art will readily appreciate that many modifications are possible in the examples without materially departing from solid state lasers. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

What is claimed is:

1. A downhole production logging tool for analyzing a formation fluid, the tool comprising:
    a tool housing comprising a window; and
    an optical module comprising:
        a light source configured to output light, wherein the light source comprises a solid state laser;
        at least one optical member configured to direct the light through the window into the formation fluid outside of the tool housing; and
        a detector configured to detect light that interacts with the formation fluid and passes back through the window,
        wherein the light that interacts with the formation fluid and passes back through the window is directed onto the detector by the at least one optical member,
    wherein the at least one optical member comprises:
        a first optical member and a second optical member configured to (i) collimate the light output by the light source and direct the light through the window into the formation fluid and (ii) direct the light that interacts with the formation fluid and passes through the window onto the detector.

2. A downhole production logging tool for analyzing a formation fluid, the tool comprising:
a tool housing comprising a window; and
an optical module comprising:
a light source configured to output light, wherein the light source comprises a solid state laser;
at least one optical member configured to direct the light through the window into the formation fluid outside of the tool housing; and
a detector configured to detect light that interacts with the formation fluid and passes back through the window, wherein the light that interacts with the formation fluid and passes back through the window is directed onto the detector by the at least one optical member, wherein the at least one optical member comprises:
at least one beam homogeneizer configured to direct and focus the light through the window into the formation fluid; and
a second optical member configured to direct the light that interacts with the formation fluid and passes through the window onto the detector wherein the beam homogenizer is a micro lens array.

3. The downhole production logging tool of claim 1 or 2, wherein the light interacting with the sample is photons scattered by a Raman band of the one or more constituents of the sample.

4. The downhole production logging tool of claim 1 or 2, wherein the window is a distance from the sample and the distance is less than three times an inverse of an absorption coefficient of the sample at a wavelength of light to be scattered by the sample.

5. The downhole production logging tool of claim 1 or 2, wherein the light source comprises a pulsed laser.

6. The downhole production logging tool of claim 1 or 2, wherein the optical module is a Raman spectrometer.

7. The downhole production logging tool of claim 1 or 2, wherein the window comprises sapphire.

8. The downhole production logging tool of claim 1 or 2, wherein the formation fluid comprises gas.

\* \* \* \* \*